(12) United States Patent
Jay

(10) Patent No.: US 6,960,562 B2
(45) Date of Patent: Nov. 1, 2005

(54) TRIBONECTIN POLYPEPTIDES AND USES THEREOF

(75) Inventor: Gregory D. Jay, Norfolk, MA (US)

(73) Assignee: Rhode Island Hospital, A Lifespan Partner, Providence, RI (US)

( * ) Notice: Subject to any disclaimer, the term of this patent is extended or adjusted under 35 U.S.C. 154(b) by 430 days.

(21) Appl. No.: 09/897,188

(22) Filed: Jul. 2, 2001

(65) Prior Publication Data

US 2004/0072741 A1 Apr. 15, 2004

Related U.S. Application Data

(63) Continuation-in-part of application No. 09/556,246, filed on Apr. 24, 2000, and a continuation-in-part of application No. 09/298,970, filed on Apr. 23, 1999, now Pat. No. 6,743,774.

(51) Int. Cl.[7] .................. A61K 38/16; A61K 38/00; C07K 1/00; C07K 14/00

(52) U.S. Cl. ................. 514/8; 530/395; 530/350; 530/300

(58) Field of Search ................ 530/300, 350, 530/395; 514/8

(56) References Cited

U.S. PATENT DOCUMENTS

| | | | |
|---|---|---|---|
| 2,487,377 A | 11/1949 | Roehner et al. | 252/42.11 |
| 2,734,862 A | 2/1956 | Morway et al. | 252/14 |
| 2,878,184 A | 3/1959 | March et al. | 252/15 |
| 4,108,849 A | 8/1978 | Thomas | 260/122 |
| 4,438,100 A | 3/1984 | Balslev et al. | 424/104 |
| 5,260,417 A | 11/1993 | Grant et al. | 530/351 |
| 5,326,558 A | 7/1994 | Turner et al. | 424/85.1 |
| 5,510,121 A | 4/1996 | Rhee et al. | 424/520 |
| 5,510,122 A | 4/1996 | Sreebny et al. | 424/537 |
| 5,515,590 A | 5/1996 | Pienkowski | 29/404 |
| 5,612,028 A | 3/1997 | Sackier et al. | 424/93.7 |
| 5,639,796 A | 6/1997 | Lee | 514/773 |
| 5,702,456 A | 12/1997 | Pienkowski | 623/18 |
| 5,709,020 A | 1/1998 | Pienkowski et al. | 427/2.26 |
| 6,433,142 B1 * | 8/2002 | Turner et al. | 530/351 |

FOREIGN PATENT DOCUMENTS

WO    WO 92/13075    8/1992

OTHER PUBLICATIONS

Gesner et al. Alignment result attached. #1.*
Gesner et al. Alignment result attached. #2.*
Gesner et al. Alignment result attached. #3.*
Gesner et al. Alignment result attached. #4.*
Gesner et al. Alignment result attached. #5.*
Gesner et al. Alignment result attached. #6.*
Aydelotte et al. (1992) "Heterogencity of Articular Chondrocytes", *Articular Cartilage and Osteoarthritis*, Raven Press Ltd., New York, pp. 237–249.

J.P. Caron (1992) "Understanding the Pathogenesis of Equine Osteoarthritis", *Br. Vet.JSci.* USA, vol. 149, pp. 369–371.

Flannery et al. (1999) "Articular Cartilage Superficial Zone Protein (SZP) is Homologous to Megakaryocyte Stimulating Factor Precursor and is a Multifunctional Proteoglycan with Potential Growth–Promoting, Cytoprotective, anmd Lubricating Properties in Cartilage Metabolism", *Biochemical and Biophysical Communications*, vol. 254, pp. 535–541.

Garg et al (1979) "The Structure of the O–Glycosylically–linked Oligosacharide Chains of LPG–I, A Glycoprotein Present in Articular Lubricating Fraction of Bovine Synovial Fluid" *Carbohydrate Research*, vol. 78, pp. 79–88.

Jay (1992) "Characterization of a Bovine Synovial Fluid Lubricating Factor. I. Chemical, Surface Activity and Lubricating Properties" *Connective Tissue Research*, vol. 28, pp. 71–88.

Jay et al. (1992) "Characterization of a Bovine Synovial Fluid Lubricating Factor. II. Comparison with Purified Ocular and Salivary Mucin" *Connective Tissue Research*, vol. 28, pp. 89–98.

Jay et al. (1992) "Characterization of a Bovine Synovial Fluid Lubricating Factor. III. The Interaction with Hyaluronic Acid" *Connective Tissue Research*, vol. 28, pp. 245–255.

Jay et al. (1990) "Silver Staining of Extensively Glycosylated Proteins on Sodium Dodecyl Sulfate–Polyacrylamide Gels: Enhancement by Carbohydrate–Binding Dyes", *Analytical Biochemistry*, vol. 185, pp. 324–330.

Jay et al. (1998) "Comparison of the Boundary–Lubricating Ability of Bovine Synovial Fluid, Lubricin, and Healon", J Biomed Mater Res, vol. 40, pp. 414–418.

Jay (1990), "Joint Lubrication: A Physicochemical Study of a Purified Lubrication Factor from Bovine Synovial Fluid", Thesis, Degree of Doctor of Philosophy, Basis Health Sciences (Cellular and Molecular Pathology), State University of New York.

Jay et al. (2000) "Lubricin is a product of megaryocyte stimulating factor gene expression by human synovial fibroblasts", *J. Rheumatology*, vol. 27, No. 3, pp. 594–600.

Lorenzo et al. (1998) "A Novel Catilage Protein (CILP) Present in the Mid–zone of Human Articular Cartilage Increases with Age", *J of Biological Chemistry*, vol. 273, No. 36, pp. 23463–23468.

(Continued)

Primary Examiner—Jon Weber
Assistant Examiner—Rita Mitra
(74) *Attorney, Agent, or Firm*—Clark & Elbing, LLP; Paul T. Clark

(57) ABSTRACT

The invention features a lubricating polypeptide and methods of lubricating joints or other tissues by administering the polypeptide systemically or directly to tissues.

5 Claims, 2 Drawing Sheets

OTHER PUBLICATIONS

Lorenzo et al. (1998) "Cloning and Deduced Amino Acid Sequence of a Novel Cartilage Protein (CILP) Identifies a Proform Including a Nucleotide Pyrophosphohydrolase", *J of Biological Chemistry*, vol. 273, No. 36, pp. 23469–23475.

Merberg et al. (1993) "A Comparison of Vitronectin and Megakaryocyte Stimulating Factor", Elevier Science Publishers, B.V., pp. 45–53.

Merberg et al. (1997) "Megakaryocyte Stimulating Factor", EMBL Sequence Database Accession No. Q92954.

Merberg et al. (1997) "Human Megakaryocyte Stimulating Factor mRNA, complete cds", EMBL Sequence Database Accession No. U70136.

Schumacher et al. (1999) "Immunodetection and Partial cDNA Sequence of the Proteoglycan, Superficial Zone Protein, Synthesized by Cells Lining Synovial Joints", *J Orthopaedic Research*, vol. 17, pp. 110–121.

Schumacher et al. (1994) "A Novel Proteoglycan Synthesized and Secreted by Chondrocytes of the Superficial Zone of Articular Cartilage", *Archives of Biochemistry and Biophysics*, vol. 311, pp. 144–152.

Swann et al. (1985) "The Molecular Structure and Lubricating Activity of Lubricin Isolated from Bovine and Human Synovial Fluids", *Biochem J*, vol. 225, pp. 195–201.

Swann et al. (1981) "The Molecular Structure of Lubricating Glycoprotein–I, the Boundary Lubricant for Articular Cartilage", *J. Biological Chemistry*, vol. 256, No. 11, pp. 5921–5925.

Turner et al. (1991) "Purification, Biochemical Characterization, and Cloning of a Novel Megakaryocyte Stimulating Factor that has Megakaryocyte Colony Stimulating Activity", Blood, vol. 78 (Suppl. 1), pp. 279.

* cited by examiner

```
            502         630
V1  ATA ACA GAA [GAA···AAA] GTA AAA GAT AAC exon 4                      exon 6
      I¹⁵⁴ T¹⁵⁵ E¹⁵⁶              V²⁰⁰ K   D  N²⁰³

352         630
V2  TGT GCA GAA [GTG···AAA] GTA AAA GAT AAC exon 3                      exon 6
      C¹⁰⁴ A¹⁰⁵ E¹⁰⁶              V²⁰⁰ K   D  N²⁰³

109        231         352        630
V3  TCA TCT CAA [GAT...GCG] GAG···GAA [GTG···AAA] GTA AAA GAT AAC exon 1              exon 3              exon 6
      S²³ S²⁴ Q²⁵         E⁶⁷ ··· E¹⁰⁶         V²⁰⁰ K   D  N²⁰³
```

Fig. 2

TRIBONECTIN POLYPEPTIDES AND USES THEREOF

This application is a continuation in part of U.S. application Ser. No. 09/556,246, filed on Apr. 24, 2000, which is a continuation in part of U.S. application Ser. No. 09/298970, filed on Apr. 23, 1999, issued as U.S. Pat. No. 6,743,774, on Jun. 1, 2004, which is incorporated herein by reference in its entirety.

BACKGROUND OF THE INVENTION

The invention relates to lubrication of mammalian joints.

Osteoarthritis (OA) is the one of the most common form of joint disease. Factors which contribute to the development of OA include a family history of OA, previous damage to the joint through injury or surgery, and age of the joint, i.e., "wear and tear" of the articulating surfaces of the joint. OA is very common in older age groups, but can affect children as well.

Current treatment is directed to relieving pain and other symptoms of OA, e.g., by administering analgesics and anti-inflammatory drugs. Other therapeutic approaches include viscosupplementation by administering hyaluronic acid and derivatives thereof to joint tissue to increase the viscosity of synovial fluid.

SUMMARY OF THE INVENTION

The invention features a novel treatment for osteoarthritis and other degenerative joint diseases by tribosupplementation. Tribosupplementation is carried out by administering lubricating polypeptides directly to the injured or arthritic joint. Unlike viscosupplementation, tribosupplementation does not substantially increase the viscosity of the solution, e.g., synovial fluid, to which it is added. The viscosity of a solution to which a tribonectin is added increases no more than 10%, preferably no more than 5%, more preferably no more than 2%, more preferably no more than 1%. Most preferably, the viscosity of the solution to which a tribonectin is added is unaltered or decreases.

Accordingly, the invention provides a tribonectin. A tribonectin is an lubricating polypeptide, which contains at least one repeat of an amino acid sequence which is at least 50% identical to KEPAPTT (SEQ ID NO:3). A tribonectin contains at least one O-linked lubricating moiety. Preferably the lubricating moiety is a β(1–3)Gal-GalNAc moiety. Optionally, the β(13)Gal-GalNAc is capped with NeuAc. The polypeptide contains an oligosaccharide, which is moiety is N-linked to an asparagine residue, e.g., the oligosaccharide is asialo-, digalactosylated bi-antennary, bisecting N-acteylglucosamine, tri-mannosyl core-fucosylated.

The amino acid sequence of the protein backbone of a lubricating polypeptide may differ depending on alternative splicing of exons of the human megakaryocyte stimulating factor (MSF) gene. Tribonectins are purified naturally-occurring polypeptides or synthetically produced or recombinant polypeptides. Optionally, the polypeptide compositions do not contain a lipid. For example, less than 10%, preferably less than 5%, and more preferably less than 1% of the lubricating polypeptide composition is a lipid. Preferably, the polypeptide compositions are purified from fibronectin. For example, less than 10%, preferably less than 5%, and more preferably less than 1% of the lubricating polypeptide composition is a fibronectin.

The amino acid sequence of the backbone of purified, synthetic, or recombinant tribonectins is at least 50% identical to the amino acid sequence of a naturally-occurring tribonectin and possess at least 50% of the lubricating activity of a naturally-occurring tribonectin.

A lubricating polypeptide contains amino acids 67–106 and 200–1140 of SEQ ID NO:1 and at least one O-linked oligosaccharide, but lacks amino acids 26–66 of SEQ ID NO:1.

Optionally, the polypeptide further lacks amino acids 107–156 of SEQ ID NO:1 or amino acids 107–199 of SEQ ID NO:1. For example, the polypeptide contains amino acids 1–25, 67–106, and 200–1404 of SEQ ID NO:1. Alternatively, the polypeptide contains amino acids 67–106 and 200–1140 of SEQ ID NO:1 and at least one O-linked oligosaccharide, but lacks amino acids 107–156 of SEQ ID NO:1. In another variation, the lubricating polypeptide contains amino acids 67–106 and 200–1140 of SEQ ID NO:1 and at least one O-linked oligosaccharide, but lacks amino acids 157–199 of SEQ ID NO:1. For example, the polypeptide contains amino acids 1–156 and 200–1404 of SEQ ID NO:1 (lacking amino acids 157–199 of SEQ ID NO:1) or the polypeptide contains amino acids 1–106 and 200–1404 (lacking amino acids 107–199 of SEQ ID NO:1). The amino acid sequences are contiguous to one another or may be separated by intervening unrelated sequences. Preferably, the lubricating polypeptide contains residues encoded by exons 1, 3, and 6–12 of the MSF gene.

The invention also includes polynucleotides encoding the polypeptide backbone of a lubricating polypeptide. For example, the nucleotide sequence contains nucleotides 232–351 and 631–3453 of SEQ ID NO:2 and lacks nucleotides 109–231 of SEQ ID NO:2. In another example, the polynucleotide contains nucleotides 232–351 and 631–3453 of SEQ ID NO:2 and lacks nucleotides 352–501 of SEQ ID NO:2. In yet another examples, the polynucleotide contains nucleotides 232–351 and 631–3453 of SEQ ID NO:2 and lacks nucleotides 502–630 of SEQ ID NO:2. A polynucleotide containing nucleotides 232–351 and 631–3453 of SEQ ID NO:2 and lacking nucleotides 352–630 of SEQ ID NO:2 is also within the invention as well as a polynucleotide containing nucleotides 232–351 and 631–3453 of SEQ ID NO:2 and lacking nucleotides 109–231 and 352–630 of SEQ ID NO:2. For example, the polynucleotide contains nucleotides 34–501 linked in-frame to nucleotides 631–4245 of SEQ ID NO:2 or nucleotides 34–501 linked in-frame to nucleotides 631–4245 of SEQ ID NO:2. The polynucleotide contains a first sequence containing nucleotides 34–501 of SEQ ID NO:2, a second sequence containing nucleotides 232–351 of SEQ ID NO:2, and a third sequence containing nucleotides 631–4245 of SEQ ID NO:2. The first, second and third sequences are linked in-frame. Preferably, the sequences described above are contiguous.

A tribonectin is formulated for administration to a mammalian joint or other tissue, e.g., cardiac tissue, for which lubrication is desired. Accordingly, a method of reducing a symptom of Camptodactyl-arthropathy-pericarditis syndrome (CAP) in a mammal is carried out by administering to the mammal a MSF polypeptide, an alternatively spliced polypeptide variant thereof, or polynucleotides encoding MSF or alternatively spliced MSF variants. The mammal is suffering from or at risk of developing CAP. The invention also includes a method of reducing a symptom of osteoarthritis in a mammal by administering the polypeptides or polynucleotides described above.

Preferably, the tribonectin is a recombinant or chemically-synthesized lubricating polypeptide. For example, a tribonectin includes a substantially pure polypeptide the amino acid sequence of which includes at least one repeats but less than 76 repeats. Each subunit contains at least 7 amino acids (and typically, 10 or fewer amino acids). The amino acid sequence of each subunit is at least 50% identical to SEQ ID NO:3, and a non-identical amino acid in the reference sequence is a conservative amino acid substitution. For example, one or both of the threonine residues are substituted with a serine residue. Preferably, the amino acid sequence of the subunit is identical to SEQ ID NO:3. The tribonectin may also contain one or more repeats of the amino acid sequence XXTTTX (SEQ ID NO:4). In the domain encoded by exon 3 of the MSF gene (amino acids 67–106 of SEQ ID NO:1), the cysteine residues are preferably conserved, i.e., not substituted with another amino acid.

Polypeptides or other compounds described herein are said to be "substantially pure" when they are within preparations that are at least 60% by weight (dry weight) the compound of interest. Preferably, the preparation is at least 75%, more preferably at least 90%, and most preferably at least 99%, by weight the compound of interest. Purity can be measured by any appropriate standard method, for example, by column chromatography, polyacrylamide gel electrophoresis, or HPLC analysis.

Where a particular polypeptide or nucleic acid molecule is said to have a specific percent identity to a reference polypeptide or nucleic acid molecule of a defined length, the percent identity is relative to the reference polypeptide or nucleic acid molecule. Thus, a peptide that is 50% identical to a reference polypeptide that is 100 amino acids long can be a 50 amino acid polypeptide that is completely identical to a 50 amino acid long portion of the reference polypeptide. It can also be a 100 amino acid long-polypeptide which is 50% identical to the reference polypeptide over its entire length.

A polypeptide or nucleic acid molecule which is "substantially identical" to a given reference polypeptide or nucleic acid molecule is a polypeptide or nucleic acid molecule having a sequence that has at least 85%, preferably 90%, and more preferably 95%, 98%, 99% or more identity to the sequence of the given reference polypeptide sequence or nucleic acid molecule. "Identity" has an art-recognized meaning and is calculated using well known published techniques, e.g., Computational Molecular Biology, 1988, Lesk A. M., ed., Oxford University Press, New York; Biocomputing: Informatics and Genome Projects, 1993, Smith, D. W., ed., Academic Press, New York; Computer Analysis of Sequence Data, Part I, 1994, Griffin, A. M. and Griffin, E. G., eds., Eumana Press, New Jersey; Sequence Analysis in Molecular Biology, 1987, Heinje, G., Academic Press, New 20 York; and Sequence Analysis Primer, 1991, Gribskov, M. and Devereux, J., eds., Stockton Press, New York). While there exist a number of methods to measure identity between two polynucleotide or polypeptide sequences, the term "identity" is well known to skilled artisans and has a definite meaning with respect to a given specified method. Sequence identity described herein is measured using the Lasergene software package (DNASTAR, Inc. Madison, Wis.). The MegAlign module used is the Clustal V method (Higgins et al. 1989, CABIOS 5 (2):151–3. The parameters used are gap penalty 10, gap length penalty 10.

Alternatively, nucleic acids which differ from a given reference sequence hybridize at high stringency to a stand of DNA having the reference sequence or the complement thereof. High stringency conditions are hybridization at 42 degrees C. in 50% formamide, a first wash at 65 degrees C in 2×SSC and a second wash at 65 degrees C. in 0.2×SSC.

A tribonectin is characterized as reducing the coefficient of friction ($\mu$) between bearing surfaces. For example, reduction of friction is measured in vitro by detecting a reduction in friction in a friction apparatus using latex:glass bearings. Reduction of friction is also measured in vivo, e.g., by measuring reduction of patient pain. Tribonectins of the invention are lubricating compositions. Polypeptides that have at least 50% (but less than 100%) amino acid sequence identity to a reference sequence are tested for lubricating function by measuring a reduction in the $\mu$ between bearing surfaces.

A tribonectin includes an O-linked oligosaccharide, e.g., an N-acetylgalactosamine and galactose in the form beta (1–3)Gal-GalNAC. For example, KEPAPTT (SEQ ID NO:3) and XXTTTX (SEQ ID NO:4) repeat domains are glycosylated by beta (1–3)Gal-GalNAC (which may at times be capped with NeuAc in the form of $\beta$(1–3) Gal-GalNAC-NeuAc. The term "glycosylated" with respect to a polypeptide means that a carbohydrate moiety is present at one or more sites of the polypeptide molecule. For example, at least 10%, preferably at least 20%, more preferably at least 30%, and most preferably at least 40% of the tribonectin is glycosylated. Up to 50% or more of the tribonectin can be glycosylated. Per cent glycosylation is determined by weight. For example, a tribonectin polypeptide is 50% (w/w) glycosylated with O-linked $\beta$(1–3)Gal-GalNAc oligosaccharides capped with NeuAc.

A tribonectin polypeptide contains a substantially pure fragment of MSF. For example, the molecular weight of a substantially pure tribonectin having an amino acid sequence of a naturally-occurring tribonectin is in the range of 220–280 kDa. Preferably, the apparent molecular weight of a tribonectin is less than 230 kDa, more preferably less than 250 kDa, and most preferably less than 280 kDa. A protein or polypeptide fragment is defined as a polypeptide which has an amino acid sequence that is identical to part, but not all, of the amino acid sequence of a naturally-occurring protein or polypeptide from which it is derived, e.g., MSF. The tribonectin may contain a polypeptide, the amino acid sequence of which is at least 50% identical to the sequence of residues 200–1140, inclusive, of SEQ ID NO:1, e.g., it contains the amino acid sequence of residues 200–1140, inclusive, of SEQ ID NO:1. In another example, the polypeptide contains an amino acid sequence that is at least 50% identical to the sequence of residues 200–1167, inclusive, of SEQ ID NO:1, e.g., one having the amino acid sequence identical to residues 200–1167, inclusive, of SEQ ID NO:1. The polypeptide contains an amino acid sequence that is at least 50% identical to the sequence of residues 200–1212, inclusive, of SEQ ID NO:1, e.g., the amino acid sequence of residues 200–1212, inclusive, of SEQ ID NO:1, or the polypeptide contains an amino acid sequence that is at least 50% identical to the sequence of residues 200–1263, inclusive, of SEQ ID NO:1, e.g., an amino acid sequence identical to residues 200–1263, inclusive, of SEQ ID NO:1.

The invention also features an isolated nucleic acid molecule encoding a tribonectin. For example, the nucleic acid includes a sequence that is at least 50% identical to nucleotides 631–3453, inclusive, of SEQ ID NO:2. Preferably, the nucleic acid encodes a polypeptide with the amino acid sequence of residues 200–1140 of SEQ ID NO:1. For example, the nucleic acid has a nucleotide sequence identical to that of nucleotides 631–3453, inclusive, of SEQ ID NO:2, or a degenerate variant thereof. An isolated nucleic acid molecule is a nucleic acid molecule that is separated from the 5' and 3' coding sequences or non-coding sequences with which it is immediately contiguous in the naturally occurring genome of an organism. Isolated nucleic acid molecules include nucliic acid molecules which are not naturally occurring, e.g., nucleic acid molecules created by recombinant DNA techniques. For example, the nucleic acid of the invention includes nucleotides 631–3453, inclusive, of SEQ ID NO:2, but not nucleotides which are immediately contiguous to those sequences in the naturally-occurring genomic sequence or naturally-occurring cDNA.

Also within the invention is a method of lubricating a mammalian joint by contacting the joint with purified MSF or a tribonectin. The mammal is preferably a human, horse, dog, ox, donkey, mouse, rat, guinea pig, cow, sheep, pig, rabbit, monkey, or cat, and the joint is an articulating joint such as a knee, elbow, shoulder, hip, or any other weight-bearing joint. Tribonectins are administered intra-articularly. Therapeutic joint lubrication is also carried out by gene therapy, e.g., by contacting the joint or synovial fluid with a nucleic acid encoding a tribonectin. For example, nucleic acids are administered to a synovial cavity by intra-articular injection.

In addition to functioning as a boundary lubricant in a mammalian joint, a tribonectin is used as a boundary lubricant between soft mammalian tissues such as skin or internal organs or between a mammalian tissue and a medical device such as a prosthetic implant. Accordingly, the invention encompasses a biocompatible composition containing a tribonectin in a form suitable for the inhibition of tissue adhesion formation. For example, the tribonectin is in the form of a film, membrane, foam, gel, or fiber. The term "film," as used herein, means a substance formed by compressing a foam or gel to a thin membrane, e.g., by casting into a flat mold and air drying to a thin membrane, or by compressing a gel or fibers, or by allowing or causing a gel or fibers to dehydrate. The term "foam," as used herein, means a substance with a porous structure formed, e.g., by introduction of as air into a tribonectin solution, suspension, gels, or fiber. The term "bioabsorbable," as used herein, refers to the ability of a tissue-compatible material to degrade in the body after implantation, into nontoxic products which are eliminated from the body or metabolized. A "biocompatible" substance, as the term is used herein, is one that has no medically unacceptable toxic or injurious effects on biological function. Tribonectin compositions for the prevention of adhesions are also formulated as compositions suitable for extrusion, e.g., to form a mold upon which tissue can grow without adhering.

A method inhibiting adhesion formation between a first surface and a second surface in a mammal is carried out by placing a tribonectin between the first and second surfaces in an amount sufficient to prevent adhesion of the surfaces in the mammal. For example, one or both of the surfaces is a mammalian tissue, and a tribonectin placed between them prevents formation of adhesions during the healing process. Alternatively the first or the second surface (or both) is an artificial device such as an orthopedic implant. Tissues to be treated include those injured by surgical incision or trauma.

Also within the invention is a method for diagnosing osteoarthritis or a predisposition thereto by obtaining a biological sample from a mammal and measuring the amount of an MSF fragment in the biological sample. An increase in the amount compared to a control, e.g., a predetermined value associated with a negative diagnosis or a biological sample from a mammal known to be free of osteoarthritis, indicates that the mammal suffers from osteoarthritis or is predisposed to developing osteoarthritis. Any biological sample is suitable for testing in the diagnostic method; typically, the biological sample is synovial fluid, blood, serum, or urine. Preferably, the MSF fragment contains the amino acid sequence of SEQ ID NO:3. Alternatively, the MSF fragment contains the amino acid sequence of EPAPTT (SEQ ID NO:5; a product of trypsin cleavage of a tribonectin) or the amino acid sequence of PTTKEP (SEQ ID NO:6; a product of elastase cleavage of a tribonectin).

Other features and advantages of the invention will be apparent from the following description of the preferred embodiments thereof, and from the claims.

BRIEF DESCRIPTION OF THE DRAWINGS

FIG. 1A graphically shows MSF exons expressed in tribonectin isoforms. FIG. 1B schematically shows exon expression in articular chondrocytes compared to synovial fibroblasts Exons 2, 4, and 5 are alternatively spliced resulting in isoform expression.

FIG. 2 is a diagram showing the alternative splicing boundaries of tribonectin isoforms V1, V2, and V3.

DETAILED DESCRIPTION

Figures 1A, 1B:
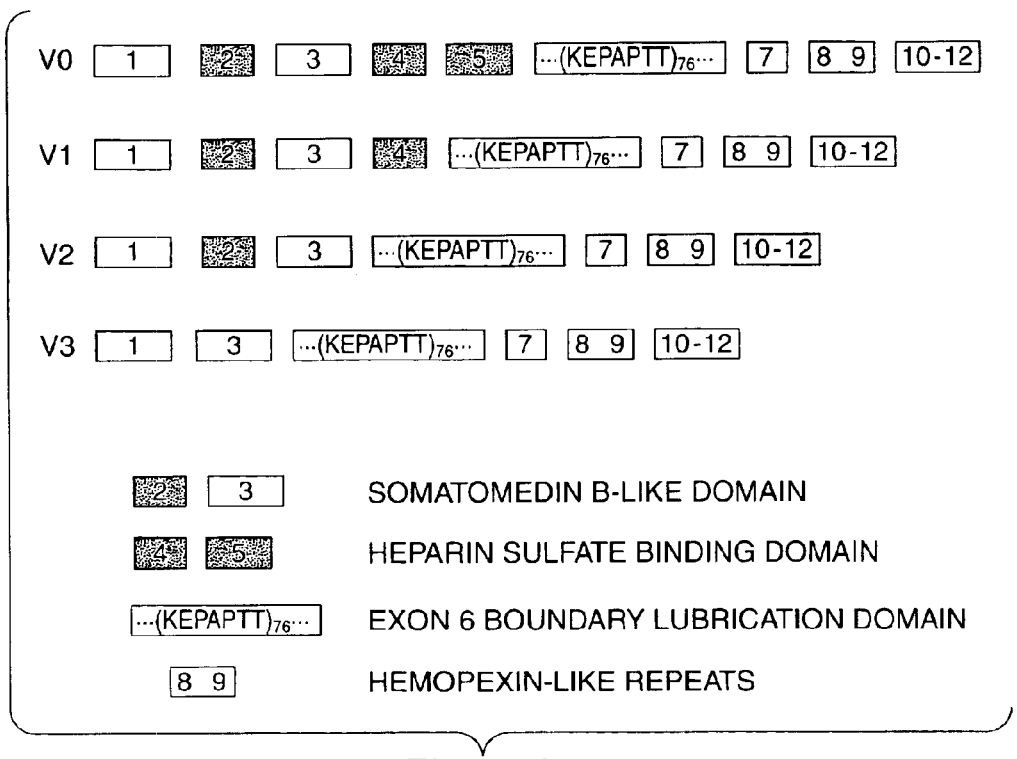
FIGS. 1A–B are diagrams of phenotypic isoforms of tribonectin expression by human synovial fibroblasts and articular chondrocytes, respectively.

A number of naturally-occurring tribonectin isoforms were identified and isolated. For example, a human lubricating polypeptide was purified from synovial fluid and found to contain amino acids encoded by exons 1, 3, and 6–12 of the MSF gene (but may lack exon 2, 4, or 5). The gene encoding naturally-occurring full length MSF contains 12 exons, and the naturally-occurring MSF gene product contains 1404 amino acids with multiple polypeptide sequence homologies to vitronectin including hemopexin-like and somatomedin-like regions. Centrally-located exon 6 contains 940 residues. Exon 6 encodes a O-glycosylated mucin domain. A polypeptide encoded by nucleotides 631–3453 of SEQ ID NO:2 provides boundary lubrication of articular cartilage.

TABLE 1

MSF amino acid sequence (SEQ ID NO:1)

MAWKTLPIYLLLLLSVFVIQQVSSQDLSSCAGRCGEGYSRDATCNCDYNC

QHYMECCPDFKRVCTAELSCKGRCFESFERGRECDCDAQCKKYDKCCPDY

ESFCAEVHNPTSPPSSKKAPPPSGASQTIKSTTKRSPKPPNKKKTKKVIE

SEEITEEHSVSENQESSSSSSSSSSSSSTIWKIKSSKNSAANRELQKKLKV

KDNKKNRTKKKPTPKPPVVDEAGSGLDNGDFKVTTPDTSTTQHNKVSTSP

KITTAKPINPRPSLPPNSDTSKETSLTVNKETTVETKETTTTNKQTSTDG

KEKTTSAKETQSIEKTSAKDLAPTSKVLAKPTPKAETTTKGPALTTPKEP

TPTTPKEPASTTPKEPTPTTIKSAPTTPKEPAPTTTKSAPTTPKEPAPTT

TKEPAPTTPKEPAPTTTKEPAPTTTKSAPTTPKEPAPTTPKKPAPTTPKE

PAPTTPKEPTPTTPKEPAPTTKEPAPTTPKEPAPTAPKKPAPTTPKEPAP

TTPKEPAPTTTKEPSPTTPKEPAPTTTKSAPTTTKEPAPTTTKSAPTTPK

EPSPTTTKEPAPTTPKEPAPTTPKKPAPTTPKEPAPTTPKEPAPTTTKKP

APTAPKEPAPTTPKEPTAPTTPKKLTPTTPEKLAPTTPEKPAPTTPEELA

PTTPEEPTPTTPEEPAPTTPKAAAPNTPKEPAPTTPKEPAPTTPKEPAPT

TPKETAPTTPKGTAPTTLKEPAPTTPKKPAPKELAPTTTKEPTSTTSDKP

TABLE 1-continued

MSF amino acid sequence (SEQ ID NO:1)

APTTPKGTAPTTPKEPAPTTPKEPAPTTPKGTAPTTLKEPAPTTPKKPAP

KELAPTTTKGPTSTTSDKPAPTTPKETAPTTPKEPAPTTPKKPAPTTPET

PPPTTSEVSTPTTTKEPTTIHKSPDESTPELSAEPTPKALENSPKEPGVP

TTKTPAATKPEMTTTAKDKTTERDLRTTPETTTAAPKMTKETATTTEKTT

ESKJTATTTQVTSTTTQDTTPFKITTLKTTTLAPKVTTTKKTITTTEIMN

KPEETAKPKDRATNSKATTPKPQKPTKAPKKPTSTKKPKTMPRVRKPKTT

PTPRKMTSTMPELNPTSRIAEAMLQTTTRPNQTPNSKLVEVNPKSEDAGG

TABLE 1-continued

MSF amino acid sequence (SEQ ID NO:1)

AEGETPHMLLRPHVFMPEVTPDMDYLPRVPNQGIIINPMLSDETNICNGK

PVDGLTTLRNGTLVAFRGHYFWMLSPFSPPSPARRITEVQGIPSPIDTVF

TRCNCEGKTFFFKDSQYWRFTNDIKDAGYPKPIFKGFGGLTGQIVAALST

AKYKNWPESVYFFKRGGSIQQYIYKQEPVQKCPGRRPALNYPVYGEMTQV

RRRRFERAIGPSQTHTIRIQYSPARLAYQDKGVLHNEVKVSILWRGLPNV

VTSAISLPNIRKPDGYDYYAFSKDQYYNIDVPSRTARAITTRSGQTLSKV

WYNCP

TABLE 2

MSF cDNA (SEQ ID NO:2)

```
   1 gcggccgcga ctattcggta cctgaaaaca acgatggcat ggaaaacact tcccatttac
  61 ctgttgttgc tgctgtctgt tttcgtgatt cagcaagttt catctcaaga tttatcaagc
 121 tgtgcaggga gatgtgggga agggtattct agagatgcca cctgcaactg tgattataac
 181 tgtcaacact acatggagtg ctgccctgat ttcaagagag tctgcactgc ggagctttcc
 241 tgtaaaggcc gctgctttga gtccttcgag agagggaggg agtgtgactg cgacgcccaa
 301 tgtaagaagt atgacaagtg ctgtcccgat tatgagagtt tctgtgcaga agtgcataat
 361 cccacatcac caccatcctt aaagaaagca cctccacctt caggagcatc tcaaaccatc
 421 aaatcaacaa ccaaacgttc acccaaacca ccaaacaaga agaagactaa gaaagttata
 481 gaatcagagg aaataacaga gaacattct gtttctgaaa atcaagagtc ctcctcctcc
 541 tcctcctctt cctcttcttc ttcaacaatt tggaaaatca gttttccaa aaattcagct
                                                EXON 6
 601 gctaatagag aattacagaa gaaactcaaa gtaaaagata acaagaagaa cagaactaaa
 661 aagaaaccta ccccccaaacc accagttgta gatgaagctg gaagtggatt ggacaatggt
 721 gacttcaagg tcacaactcc tgacacgtct accacccaac acaataaagt cagcacatct
 781 cccaagatca caacagcaaa accaataaat cccagaccca gtcttccacc taattctgat
 841 acatctaaag agacgtcttt gacagtgaat aaagagacaa cagttgaaac taaagaaact
 901 actacaacaa ataaacagac ttcaactgat ggaaaagaga agactactc cgctaaagag
 961 acacaaagta tagagaaaac atctgctaaa gatttagcac ccacatctaa agtgctggct
1021 aaacctacac ccaaagctga aactacaacc aaaggccctg ctctcaccac tcccaaggag
1081 cccacgccca ccactccaa ggagcctgca tctaccacac ccaaagagcc cacacctacc
1141 accatcaagt ctgcacccac cacccccaag gagcctgcac ccaccaccac caagtctgca
1201 cccaccactc ccaaggagcc tgaacccacc accaccaagg agcctgcacc caccactccc
1261 aaggagcctg cacccaccac caccaaggag cctgcaccca ccaccaa gtctgcaccc
```

TABLE 2-continued

MSF cDNA (SEQ ID NO:2)

```
1321 accactccca aggagcctgc acccaccacc cccaagaagc ctgccccaac taccccaag
1381 gagcctgcac ccaccactcc caaggagcgc acacccacca ctcccaagga gcctgcaccc
1441 accaccaagg agcctgcacc caccactccc aaagagcttg cacccactgc ccccaagaag
1501 cctgcccaaa ctaccccaa ggagcctgca cccaccactc caaggagcc tgcacccacc
1561 accaccaagg agccttcacc caccactccc aaggagcctg caccaccac caccaagctc
1621 gcacccacca ctaccaagga gcctgcaccc accactacca agtctgcacc caccactccc
1681 aaggagcctt cacccaccac caccaaggag cctgcaccca ccactcccaa ggagcctgca
1741 cccaccaccc caagaagcc tgcccaact accccaagg agcctgcacc caccactccc
1801 aaggaacctg cacccaccac caccaagaag cctgcagcca ccgctcccaa agagcctgcc
1861 ccaactaccc caaggagac tgcacccacc acccccaaga agctcacgcc caccacccc
1921 gagaagctcg cacccaccac ccctgagaag cccgcaccca caccctga ggagctcgca
1981 cccaccaccc ctgaggagcc cacacccacc acccctgagg agcctgctcc caccactccc
2041 aaggcagcgg ctcccaacac ccctaaggag cctgctccaa ctacccctaa ggagcctgct
2101 ccaactaccc ctaaggagcc tgctccaact acccctaagg agactgctcc aactacccct
2161 aaagggactg ctccaactac cctcaaggaa cctgcaccca ctactcccaa gaagcctgcc
2221 tccaaggagc ttgcacccac caccaccaag gagcccacat ccaccacctc tgacaagccc
2281 gctccaacta cccctaaggg gactgctcca actacccta agadcctgc tccaactacc
2341 cctaaggagc ctgctccaac tacccctaag gggactgctc caactaccct caaggaacct
2401 gcacccacta ctcccaagaa gcctgcccc aaggagcttg cacccaccac caccaagggg
2461 cccacatcca ccacctctga caagcctgct ccaactacac ctaaggagac tgctccaact
2521 accccaagg agcctgcacc cactaccccc aagaagcctg ctccaactac tcctgagaca
2581 cctcctccaa ccacttcaga ggtctctact ccaactacca ccaaggagcc taccactatc
2641 cacaaaagcc ctgatgaatc aactcctgag ctttctgcag aacccacacc aaaagctctt
2701 gaaacagtc ccaaggaacc tggtgtacct acaactaaga ctcctgcagc gactaaacct
2761 gaaatgacta caacagctaa agacaagaca acagaaagag acttacgtac tacacctgaa
2821 actacaactg ctgcacctaa gatgacaaaa gagacagcaa ctacaacaga aaaactacc
2881 gaatccaaa taacagctac aaccacacaa gtaacatcta ccacaactca agataccaca
2941 ccattcaaaa ttactactct taaaacaact actcttgcac ccaaagtaac tacaacaaaa
3001 aagacaatta ctaccactga gattatgaac aaacctgaag aaacagctaa accaaaagac
3061 agagctacta attctaaagc gacaactcct aaacctcaaa agccaaccaa agcacccaaa
3121 aaaccacctt ctaccaaaaa gccaaaaaca atgctcgag tgagaaaacc aaagacgaca
3181 ccaactcccc gcaagatgac atcaacaatg ccagaattga aaccctacctc aagaatagca
3241 gaagccatgc tccaaaccac caccagacct aaccaaactc caaactccaa actagttgaa
3301 gtaaatccaa agagtgaaga tgcaggtggt gctgaaggag aaacacctca tatgcttctc
3361 aggccccatg tgttcatgcc tgaagttact cccgacatgg attacttacc gagagtaccc
3421 aatcaaggca ttatcatcaa tccatgcttt tccgatgaga ccaatatatg ccatggtaag
3481 ccagtagatg gactgactac tttgcgcaat gggacattag ttgcattccg aggtcattat
3541 ttctggatgc taagtccatt cagtccacca tctccagctc gcagaattac tgaagtttgg
```

TABLE 2-continued

MSF cDNA (SEQ ID NO:2)

```
3601 ggtattcctt cccccattga tactgttttt actaggtgca actgtgaagg aaaaactttc
3661 ttctttaagg attctcagta ctggcgtttt accaatgata taaaagatgc agggtacccc
3721 aaaccaattt tcaaaggatt tggaggacta actggacaaa tagtggcagc gctttcaaca
3781 gctaaatata agaactggcc tgaatctgtg tattttttca agagaggtgg cagcattcag
3841 cagtatattt ataaacagga acctgtacag aagtgccctg gaagaaggcc tgctctaaat
3901 tatccagtgt atggagaaat gacacaggtt aggagacgtc gctttgaacg tgctatagga
3961 ccttctcaaa cacacaccat cagaattcaa tattcacctg ccagactggc ttatcaagac
4021 aaaggtgtcc ttcataatga agttaaagtg agtatactgt ggagaggact tccaaatgtg
4081 gttacctcag ctatatcact gcccaacatc agaaaacctg acggctatga ttactatgcc
4141 ttttctaaag atcaatacta taacattgat gtgcctagta gaacagcaag agcaattact
4201 actcgttctg ggcagacctt atccaaagtc tggtacaact gtccttagac tgatgagcaa
4261 aggaggagtc aactaatgaa gaaatgaata ataaattttg acactgaaaa acattttatt
4321 aataaagaat attgacatga gtataccagt ttatatataa aaatgttttt aaacttgaca
4381 atcattacac taaaacagat ttgataatct tattcacagt tgttattgtt tacagaccat
4441 ttaattaata tttcctctgt ttattcctcc tctccctccc attgcatggc tcacacctgt
4501 aaaagaaaaa agaatcaaat tgaatatatc ttttaagaat tcaaaactag tgtattcact
4561 taccctagtt cattataaaa aatatctagg cattgtggat ataaaactgt tgggtattct
4621 acaacttcaa tggaaattat tacaagcaga ttaatccctc tttttgtgac acaagtacaa
4681 tctaaaagtt atattggaaa acatggaaat attaaaattt tacactttta ctagctaaaa
4741 cataatcaca aagctttatc gtgttgtata aaaaaattaa caatataatg gcaataggta
4801 gagatacaac aaatgaatat aacactataa cacttcatat tttccaaatc ttaatttgga
4861 tttaaggaag aaatcaataa atataaaata taagcacata tttattatat atctaaggta
4921 tacaaatctg tctacatgaa gtttacagat tggtaaatat catctgctca acatgtaatt
4981 atttaataaa actttggaac attaaaaaaa taaattggag gcttaaaaaa aaaaaaaaaa
5041 a
```

TABLE 3

MSF Exon Boundaries

| Exon | Amino acid sequence in SEQ ID NO:1 | Nucleotide sequence in SEQ ID NO:2 |
|---|---|---|
| 1 | 1–25, inclusive | 34–108, inclusive |
| 2 | 26–66, inclusive | 109–231, inclusive |
| 3 | 67–106, inclusive | 232–351, inclusive |
| 4 | 107–156, inclusive | 352–498, inclusive |
| 5 | 157–199, inclusive | 502–630, inclusive |
| 6 | 200–1140, inclusive | 631–3453, inclusive |
| 7 | 1141–1167, inclusive | 3454–3534, inclusive |
| 8 | 1168–1212, inclusive | 3535–3670, inclusive |
| 9 | 1213–1263, inclusive | 3671–3822, inclusive |
| 10 | 1264–1331, inclusive | 3823–4026, inclusive |
| 11 | 1332–1371, inclusive | 4027–4146, inclusive |
| 12 | 1372–1404, inclusive | 4147–4245, inclusive |

The boundary lubricant isolated from synovial fluid is an alternatively-spliced variant of MSF. This alternatively-spliced variant was found to be the composition present in synovial fluid that confers lubricating capabilities to the articular joint. The boundary lubricant isolated from human synovial fluid contains amino acids encoded by exons 1, 3, and 6–12 of the MSF gene. A recombinant or chemically-produced polypeptide containing at least exon 6 of MSF is useful to prevent and/or treat osteoarthritic disease. A recombinant or chemically-produced lubricating polypeptide containing at least one repeat of the amino acid sequence KEPAPTT (SEQ ID NO:3) either identically or with conservative substitution is also administered to lubricate mammalian joints.

Production and Purification of Recombinant Lubricating Polypeptides

To produce recombinant polypeptides, DNA containing exon 6 of MSF (nucleotides 631–3453 of SEQ ID NO:2) in an appropriate expression vector is transfected into a cell. The DNA can also contain some or all of exon 7 (nucleotides 354–3534 of SEQ ID NO:2), exon 8 (nucleotides 3535–3670 of SEQ ID NO:2), or exon 9 (nucleotides 3671–3822 of SEQ ID NO:2) of the MSF gene. Primers for polymerase chain reaction (PCR) methods to generate DNA which spans various exons of MSF are shown below. Other isoforms are expressed by cloning nucleic acids corresponding to the exons of MSF encoding amino acid sequences sought to be expressed.

TABLE 4

PCR Primers

| MSF exons | Forward Primer | Reverse Primer |
|---|---|---|
| Exon 2 | 5'AGATTTATCAAGCTGTG CAGGGAG3' (SEQ ID NO:7) | 5'TTTACAGGAAAGCTCCG CAGTG3' (SEQ ID NO:8) |
| Exon 6 | 5'TCAAGGTCACAACTCCT GACACG3' (SEQ ID NO:9) | 5'CTCTCGGTAAGTAATCC ATGTCG3' (SEQ ID NO:10) |
| Exons 2–12 | 5'TTGTTGCTGCTGTCTGT TTTCG3' (SEQ ID NO:11) | 5'TGGATAAGGTCTGCCCA GAACGAG3' (SEQ ID NO:12) |
| Exons 6–12 | 5'TCAAGGTCACAACTCCT GACACG3' (SEQ ID NO:13) | 5'GATGGTGTGTGTTTGAG AAGGTCC3' (SEQ ID NO:14) |

Methods of designing forward and reverse primers used to make DNAs which encode tribonectin polypeptides of varying lengths and which incorporate various exons of the MSF gene are well known in the art of molecular biology. Standard methods for transfecting cells with isolated nucleic acid are well known to those skilled in the art of molecular biology. For example, prokaryotic or eukaryotic cells in culture are transfected with the DNA of the invention operatively linked to expression control sequences appropriate for high-level expression in the cell. Such cells are useful for producing large amounts of the lubricating polypeptide, which are purified using standard methods. The lubricating polypeptides are used therapeutically for treatment or prevention of arthritic diseases. The polypeptides are also used to raise antibodies against a naturally-occurring or recombinantly produced lubricating glycoproteins or glycopeptides.

For example, the recombinant gene product is expressed as a fusion protein and purified using a commercially available expression and purification system, e.g., the pFLAG expression system (EBI). The expression systems that may be used for purposes of the invention include, but are not limited to, microorganisms such as bacteria (e.g., *E. Coli* and *B. subtilis*) transformed with recombinant bacteriophage DNA, plasmid DNA, or cosmid DNA expression vectors containing the nucleic acid molecules described herein. For production of glycosylated polypeptides, eukaryotic expression systems are used. Yeast (for example, Saccharomyces and Pichia) transformed with recombinant yeast expression vectors containing the recombinant nucleic acid encoding a tribonectin polypeptide are used. Insect cell systems infected with recombinant virus expression vectors (for example, baculovirus) containing the nucleic acid molecules encoding a tribonectin and mammalian cell systems (e.g., COS, CEO, BEK, 293, VERO, HeLa, MDCK, W138, and NIH 3T3 cells) harboring recombinant expression constructs containing promoters derived from the genome of mammalian cells (e.g., the metallothionein promoter) or from mammalian viruses (e.g., the adenovirus late promoter and the vaccinia virus 7.5K promoter) are also useful. In addition to clinical applications, recombinant polypeptides are injected into a rabbit or rodent to produce antibodies as described below.

The synovial fluid of an inflamed or injured joint contains proteolytic enzymes that degrade lubricating proteins or polypeptides. For example, infiltrating immune cells such as neutrophils secrete trypsin and/or elastase. Even a minor injury to an articulating joint or an inflammatory state can result in cellular infiltration and proteolytic enzyme secretion resulting in traumatic synovitis. Synovitis for a period of a few days or weeks can result in the loss of the cytoprotective layer of a joint, which in turn leads to the loss of cartilage. Non-lubricated cartilaginous bearings may experience premature wear which may initiate osteoarthritis. Individuals who clinically present with a traumatic effusion (e.g., "water on the knee") are predisposed to developing osteoarthritis; the elaboration of proteolytic enzymes degrades and depletes naturally-occurring lubricating compositions in the synovial fluid. Depletion of natural lubricating compositions occurs in other inflammatory joint diseases such as rheumatoid arthritis. Replacing or supplementing the synovial fluid of such injured joints with the lubricating compositions of the invention prevents the development of osteoarthritis in the long term (e.g., years, even decades later) and immediately lubricates the joint to minimize short term damage.

Analogs, homologs, or mimetics of lubricating peptides which are less susceptible to degradation in vivo are used to lubricate mammalian joints. Analogs can differ from the naturally-occurring peptides by amino acid sequence, or by modifications which do not affect the sequence, or both. Modifications (which do not normally alter primary sequence) include in vivo or in vitro chemical derivitization of polypeptides, e.g., acetylation or carboxylation. Also included are modifications of glycosylation, e.g., those made by modifying the glycosylation patterns of a polypeptide during its synthesis and processing or in further processing steps, e.g., by exposing the polypeptide to enzymes which affect glycosylation, e.g., mammalian glycosylating or deglycosylating enzymes.

Where proteolytic degradation of the peptides following injection into the subject is a problem, replacement of a particularly sensitive peptide bond with a noncleavable peptide mimetic bond renders the resulting peptide more stable, and thus more useful as a therapeutic. To render the therapeutic peptides less susceptible to cleavage by peptidases such as trypsin or elastise, the peptide bonds of a peptide may be replaced with an alternative type of covalent bond (a "peptide mimetic"). Trypsin, elastase, and other enzymes may be elaborated by infiltrating immune cells during joint inflammation. Trypsin cleaves a polypeptide bond on the carboxy-side of lysine and arginine; elastase cleaves on the carboxy-side of alanine, glycine. Thrombin, a serine protease which is present in hemorrhagic joints, cleaves a peptide bond on the carboxy-side of arginine. Collagenases are a family of enzymes produced by fibroblasts and chondrocytes when synovial metabolism is altered (e.g., during injury). These enzymes cut on the carboxy-side of glycine and proline. One or more peptidase-susceptible peptide bonds, e.g., those which appear in the KEPAPTT (SEQ ID NO:3) repeat sequence, are altered (e.g., replaced with a non-peptide bond) to make the site less susceptible to cleavage, thus increasing the clinical half-life of the therapeutic formulation.

Such mimetics, and methods of incorporating them into polypeptides, are well known in the art. Similarly, the replacement of an L-amino acid residue with a D-amino acid is a standard way of rendering the polypeptide less sensitive to proteolysis. Also useful are amino-terminal blocking groups such as t-butyloxycarbonyl, acetyl, theyl, succinyl, methoxysuccinyl, suberyl, adipyl, azelayl, dansyl, benzyloxycarbonyl, fluorenylmethoxycarbonyl, methoxyazelayl, methoxyadipyl, methoxysuberyl, and 2,4,-dinitrophenyl.

Clinical formulations of tribonectins may also contain peptidase inhibitors such as N-methoxysuccinyl-AlaAla-Pro-Val chloromethylketone (an inhibitor of elastase). Other clinically acceptable protease inhibitors (e.g., as described in Berling et al., 1998, Int. J. Pancreatology 24:9–17) such as leupeptin, aprotinin, α1-antitrypsin, α2-macroglobulin, α1-protease inhibitor, antichymotrypsin (ACHY), secretory leukocyte protease inhibitor (PSTI) are also co-administered with a tribonectin to reduce proteolytic cleavage and increase clinical halflife. A cocktail of two or more protease inhibitors can also be coadministered.

Compositions of tribonectin polypeptides or nucleic acids encoding the polypeptides are formulated in standard physiologically-compatible excipients known in the art., e.g., phosphate-buffered saline (PBS). Other formulations and methods for making such formulations are well known and can be found in, e.g., "Remington's Pharmaceutical Sciences". Tribonectins are also formulated with non-crosslinked hyaluronic acid preparations or viscosupplementation compositions, such as cross-linked hyaluronic acid preparations. When a tribonectin is added to a viscosupplement formulation, the interaction of the tribonectin with hyaluronic acid reduces the viscosity of the viscosupplement.

Methods of making a glycopeptide and determining % glycosylation are known in the art, e.g., as described in U.S. Pat. No. 5,767,254. The presence of N-acetylgalactosamine is indicative of the presence of O-linked oligosaccharides (or Ser/Thr-linked oligosaccharides) in which GalNAc is commonly found in O-glycosidic alpha-linkage directly to amino acid. The presence of O-linked oligosaccharide is also detected by binding to Jacalin-Sepharose, an immobilized plant lectin that binds to the core disaccharide sequence Gal beta (1–3) GalNAc linked to Ser/Thr in glycoproteins, or peanut agglutinin, which binds to beta (1–3) Gal-GalNAC. O-linked oligosaccharides are distinguished from N-linked oligosacharides using standard methods. For example, oligosaccharides in O-glycosidic linkage, but not in N-glycosidic linkage, are susceptible to release from peptide by treatment with mild base in the presence of sodium borohydride (50 mM NaOH, 1M NaBH$_4$, 16 hr at 45° C.) to cause a beta-elimination reaction.

Veterinary Applications

Canine osteoarthritis is a prevalent clinical disorder that is treated using the methods described herein. Osteoarthritis afflicts an estimated one in five adult dogs; an estimated 8 million dogs suffer from this degenerative, potentially debilitating disease. Yet, many owners do not recognize the signs of chronic canine pain. While any dog can develop osteoarthritis, those most at risk are large breeds, geriatric dogs, very active dogs (such as working or sporting animals), and those with inherited joint abnormalities such as hip or elbow dysplasia.

Equine degenerative joint disease such as osteoarthritis is a cause of lameness and impaired performance in horses. As with humans and other mammals, degenerative joint diseases which affect horses are progressive disorders of synovial joints characterized by articular cartilage degeneration and joint effusion. Acute or chronic trauma, overuse, developmental disease, joint instability and old age leads to synovitis, impaired chondrocyte metabolism, and the formation of fissures in the joint cartilage. Destructive enzymes such as trypsin, elastase, stromelysin and hyaluronidase are released into the joint where they degrade synovial fluid and cartilage components, resulting in decreased synovial fluid viscosity, poor lubrication, depressed cartilage metabolism and enhanced wear resulting in pain and cartilage erosion.

Current therapeutic approaches include medications for pain relief and anti-inflammatory drugs. The compositions and methods described herein are useful to replenish the lubricating capabilities of the affected joint.

Administration of Therapeutic Polypeptides

Standard methods for delivery of peptides are used. Such methods are well known to those of ordinary skill in the art. The compositions are delivered systemically or locally For intra-articular administration, tribonectin is delivered to the synovial cavity at a concentration in the range of 20–500 µg/ml in a volume of approximately 0.1–2 ml per injection. For example, 1 ml of a tribonectin at a concentration of 250 µg/ml is injected into a knee joint using a fine (e.g., 14–22 gauge, preferably 18–22 gauge) needle. The methods are used to augment tribonectin concentration in synovial fluid is to achieve a concentration of at least 15–20 mg/ml. The compositions of the invention are also useful for parenteral administration, such as intravenous, subcutaneous, intramuscular, and intraperitoneal. The composition is delivered directly to tissue in need of lubrication, e.g., locally to an articulating joint or to heart tissue.

For prevention of surgical adhesions, the tribonectins described herein are administered in the form of gel, foam, fiber or fabric. A tribonectin formulated in such a manner is placed over and between damaged or exposed tissue interfaces in order to prevent adhesion formation between apposing surfaces. To be effective, the gel or film must remain in place and prevent tissue contact for a long enough time so that when the gel finally disperses and the tissues do come into contact, they will no longer have a tendency to adhere. Tribonectins formulated for inhibition or prevention of adhesion formation (e.g., in the form of a membrane, fabric, foam, or gel) are evaluated for prevention of post-surgical adhesions in a rat cecal abrasion model (Goldberg et al., In Gynecologic Surgery and Adhesion Prevention. Willey-Liss, pp. 191–204, 1993). Compositions are placed around surgically abraded rat ceca, and compared to non-treated controls (animals whose ceca were abraded but did not receive any treatment). A reduction in the amount of adhesion formation in the rat model in the presence of the tribonectin formulation compared to the amount in the absence of the formulation indicates that the formulation is clinically effective to reduce tissue adhesion formation.

Tribonectins are also used to coat artificial limbs and joints prior to implantation into a mammal. For example, such devices are dipped or bathed in a solution of a tribonectin, e.g., as described in U.S. Pat. Nos. 5,709,020 or 5,702,456.

Lubricating polypeptides are at least about 10 amino acids (containing at least one KEPAPTT (SEQ ID NO:3) or at least one XXTTTX (SEQ ID NO:4) repeat), usually about 20 contiguous amino acids, preferably at least 40 contiguous amino acids, more preferably at least 50 contiguous amino acids, and most preferably at least about 60 to 80 contiguous amino acids in length. For example, the polypeptide is approximately 500 amino acids in length and contains 76 repeats of KEPAPTT (SEQ ID NO:3). The polypeptide is a full-length MSF polypeptide or is an MSF polypeptide that is less than 1404 residues in length, e.g., it has the amino acid sequence of naturally-occurring MSF (SEQ ID NO:1) but lacks at least 5, 10, 15, 20, or 24 amino acids of naturally-occurring MSF. Such peptides are generated by methods known to those skilled in the art, including proteolytic cleavage of a recombinant MSF protein, de novo synthesis, or genetic engineering, e.g., cloning and expression of at least exon 6, 7, 8, and/or 9 of the MSF gene.

Tribonectin polypeptides are also biochemically purified. The enzyme chymotrypsin cleaves at sites which bracket amino acids encoded by exon 6 of the MSF gene. Thus, a polypeptide containing amino acids encoded by exon of the MSF gene (but not any other MSF exons) is prepared from a naturally-occurring or recombinantly produced MSF gene product by enzymatic digestion with chymotrypsin. The polypeptide is then subjected to standard biochemical purification methods to yield a substantially pure polypeptide suitable for therapeutic administration, evaluation of lubricating activity, or antibody production.

Therapeutic compositions are administered in a pharmaceutically acceptable carrier (e.g., physiological saline). Carriers are selected on the basis of mode and route of administration and standard pharmaceutical practice. A therapeutically effective amount of a therapeutic composition (e.g., lubricating polypeptide) is an amount which is capable of producing a medically desirable result, e.g., boundary lubrication of a mammalian joint, in a treated animal. A medically desirable result is a reduction in pain (measured, e.g., using a visual analog pain scale described in Peyron et al., 1993, J. Rheumatol.(suppl.39):10–15) or increased ability to move the joint (measured, e.g., using pedometry as described in Belcher et 30 al., 1997, J. Orthop. Trauma 11:106–109). Another method to measure lubricity of synovial fluid after treatment is to reaspirate a small volume of synovial fluid from the affected joint and test the lubricating properties in vitro using a friction apparatus as described herein.

As is well known in the medical arts, dosage for any one animal depends on many factors, including the animal's size, body surface area, age, the particular compound to be administered, sex, time and route of administration, general health, and other drugs being administered concurrently. Administration is generally local to an injured or inflamed joint. Alternatively, the polypeptides are administered via a timed-release implant placed in close proximity to a joint for slow release at the site of an injured or inflamed joint.

Gene Therapy

Gene therapy is carried out by administering to a mammal a nucleic acid encoding a therapeutic lubricating polypeptide, e.g., DNA encoding one or more repeats or the amino acid sequence KEPAPTT (SEQ ID NO:3) or DNA encoding a lubricating fragment of MSF, by standard vectors and/or gene delivery systems. Suitable gene delivery systems include liposomes, receptor-mediated delivery systems, naked DNA, and viral vectors such as herpes viruses, retroviruses, adenoviruses and adeno-associated viruses.

In addition to a gene delivery system as described above, the therapeutic composition may include a pharmaceutically acceptable carrier, e.g., a biologically compatible vehicle such as physiological saline, suitable for administration to an animal. A therapeutically effective amount of a nucleic acid or polypeptide composition is an amount which is capable of producing a medically desirable result in a treated animal, e.g., a reduction in pain associated with joint movement, an increase in lubricating function of synovial fluid.

Parenteral administration, such as intravenous, subcutaneous, intramuscular, and intraperitoneal delivery routes, may be used to deliver the compound. Preferably, therapeutic compositions such as nucleic acids or polypeptides are delivered intra-articularly. Dosage for any one patient depends upon many factors, including the patient's size, body surface area, age, the particular compound to be administered, sex, time and route of administration, general health, and other drugs (e.g., anti-inflammatory drugs, viscotherapeutic drugs) being administered concurrently. A preferred dosage for administration of nucleic acids is from approximately 106 to 1022 copies of the nucleic acid molecule.

DNA is be introduced into target cells of the patient by standard vectors, e.g., a vector which contains DNA encoding a tribonectin operably linked to a promoter sequence. Suitable gene delivery systems may include liposomes, receptor-mediated delivery systems, naked DNA, and viral vectors such as herpes viruses, retroviruses, and adenoviruses, among others.

DNA may be administered locally using an adenovirus or adeno-associate virus delivery system using standard methods. For example, methods of delivering DNA intraarticularly to synovial fluid and methods of delivering DNA to cells from synovial fluid (e.g., synovial fibroblasts or chondrocytes) are described in U.S. Pat. No. 5,858,355. The only cis-acting sequences required for replication and packaging of recombinant adeno-associated virus (AAV) vector are the AAV terminal repeats. Up to 4 kb of DNA is inserted between the terminal repeats without effecting viral replication or packaging. To package a recombinant AAV vector, a plasmid containing the terminal repeats and DNA encoding a therapeutic polypeptide is co-transfected into cells with a plasmid that expresses AAV rep and capsid proteins. The transfected cells are then infected with adeno-associated virus, and recombinant AAV virus containing the desired sequences is isolated from cells approximately 48–72 hours after transfection. Recombinant virus is then administered for gene therapy applications using known methods.

Electroporation is another method of introducing DNA into target cells, e.g., synovial fibroblasts or chondrocytes, ex vivo. Cells to be electroporated are placed into Hepes buffer saline (EBS) at a concentration of about $10^7$ cells per ml. The DNA to be electroporated is added at a concentration of approximately 5–20 micrograms/ml of HBS. The mixture is placed into an electroporation device and an electric field is applied according to standard protocols, e.g., in a range of between about 250 and 300 volts. Following introduction of DNA into synovial cells ex vivo, the genetically modified autologous synovial cells are transplanted back into the donor by intra-articular injection. Approximately $10^7$ cells are injected intra-articularly into joints in a volume of approximately 1 ml.

Synovial cells into which DNA is introduced are obtained using routine methods, e.g., through an arthroscope. The arthroscope is a small, hollow rod inserted into the knee via a small puncture wound which allows access to a surgical instrument to recover synovial cells arthroscopically. In some cases, the synovial cells in arthroscopically excised tissue are aseptically recovered by enzymatic digestion of the connective tissue matrix. For example, the synovium is cut into pieces of approximately 1 mm diameter and digested sequentially with trypsin (0.2% w/v in Gey's Balanced Salt Solution) for 30 minutes at 37° C., and collagenase (0.2% w/v in Gey's Balanced Salt Solution) for 2 hours at 37° C. A suspension of genetically-modified cells is injected into a recipient mammalian joint. Intra-articular injections of this type are routine and carried out in the doctor's office without additional surgical intervention. Repeat injections are carried out as needed.

Alternatively, the DNA (naked or packaged in a virus) is formulated in a suitable pharmaceutical carrier and injected intra-articularly. Gene therapy is also administered as a prophylactic measure to prevent the development of osteoarthritis in those individuals determined to be highly susceptible of developing this disease, e.g., those who have suffered an acute joint injury. Direct intra-articular injection of a DNA encoding a therapeutic polypeptide into a joint results in transfection of the recipient synovial cells to allow expression of DNA.

Drugs which stimulate an endogenous tribonectin promoter, e.g., TGF-beta, may also be administered as described above to increase the level of synovial expression.

Production of Antibodies Specific for Synovial Lubricating Polypeptides

Antibodies specific for lubricating polypeptides are obtained by techniques well known in the art. Such antibodies can be polyclonal or monoclonal. Polyclonal antibodies can be obtained, for example, by the methods described in Ghose et al., Methods in Enzymology, Vol. 93, 326–327, 1983. For example, a lubricating polypeptide encoded by nucleotides 632–3453 of SEQ ID NO:2 is used as an immunogen to stimulate the production of polyclonal antibodies in the antisera of a rabbit. Similar methods can be used to raise antisera in animals such as goats, sheep, and rodents.

Monoclonal antibodies are obtained by the well known process described by Milstein and Kohler in Nature, 256:495–497, 1975, or as modified by Gerhard, Monoclonal Antibodies, Plenum Press, 1980, pages 370–371. Hybridomas are screened to identify those producing antibodies that are highly specific for a synovial lubricating polypeptide. Preferably, the antibody has an affinity of at least about $10^8$ liters/mole and more preferably, an affinity of at least about $10^9$ liters/mole. Monoclonal or polyclonal antibodies provide a means of rapidly purifying large quantities of recombinant lubricating polypeptides.

In addition to antibodies which are directed to the peptide core of a tribonectin, an antibody directed to a sugar portion or to a glycopeptide complex of a tribonectin is desirable. To generate an antibody to the peptide core, a peptide spanning amino acids 200–350 of SEQ ID NO:1 is used. Shorter peptides, e.g., 8–15 amino acids in length, which are identical to an 8–15 amino acid portion of amino acids 200–350 of SEQ ID NO:1 are also used to generate such antibodies. Other peptides to be used as immunogens for antibodies specific for the peptide core of a tribonectin include those which are in the region of amino acids 26–66 of SEQ ID NO:1, amino acids 105–155 of SEQ ID NO:1, or amino acids 157–199 of SEQ ID NO:1. To generate antibodies which bind to a glycosylated tribonectin polypeptide (but not a deglycosylated or nonglycosylated form), the immunogen is preferably a glycopeptide, the amino acid sequence of which spans a highly glycosylated portion of a tribonectin, e.g., a peptide with an amino acid sequence of residues 200–1140 of SEQ ID NO:1. Shorter glycopeptides, e.g., 8–15 amino acids in length, within the same highly glycosylated region are also used as immunogens. Methods of generating antibodies to highly glycosylated biomolecules are known in the art, e.g., as described by Schneerson et al., 1980, J. Exp. Med. 152:361–376.

Methods of Diagnosis

Osteoarthritis is a disease that develops slowly and is difficult to diagnose until its late stages when joint pain often compels an individual to seek medical treatment. Early diagnosis of osteoarthritis or a predisposition to develop the disease allows early intervention to prevent or reduce the development of advanced osteoarthritis. The invention provides methods of early detection of this disease or a predisposition to develop it by tasting bodily fluids such as serum or urine for the presence of fragments of naturally-occurring tribonectins or the presence of fragments of MSF. Detection and quantitation of such peptides in biological fluids is well known in the art. For example, a standard sandwich ELISA assay is carried out using two different antibodies (e.g., a first antibody which binds to an oligosaccharide portion of the glycopeptide and a second antibody which binds to the peptide core of the glycopeptide) to a naturally-occurring tribonectin. Alternatively, standard protein sequencing by liquid chromatography and mass spectroscopy, as is described below, is used to detect MSF fragments in biological samples. A control value is a predetermined value associated with a negative diagnosis; alternatively, a control sample is a biological sample from a mammal known to be free of osteoarthritis. An increase in the amount compared to a control value or sample indicates that the mammal suffers from osteoarthritis or is predisposed to developing osteoarthritis.

Characterization of a Tribonectin from Human Synovial Fluid

Aliquots of synovial fluid from patients undergoing diagnostic arthroscopy and total knee replacement were collected and assayed in the friction apparatus. In both cases, the synovial fluid was aspirated prior to initiation of any surgical procedure and immediately centrifuged at 10,000×g at 4° C. for 2 hrs to remove cellular debris. Samples which were contaminated with blood were discarded. Aliquots with normal lubricating ability were pooled and stored at –20° C.

Purification and Isolation of a Tribonectin

Human synovial fluid (200 ml) was filtered through 0.22 microsterile filter units (Nalgene) at 4° C. over two days. Retentate was scraped off filter membranes and resuspended with 50 mM NaAc buffer, pH 5.5, to the original synovial fluid volume containing proteolytic inhibitors: 1 mM phenylmethyl sulfonyl fluoride (PMSF), 1 mM parachloromercuricbenzoic acid (PCMB), and 10 mM ethylenediamine tetraacetate (EDTA). Digestion of hyaluronic acid was carried out at 37° C. by streptomyces hyaluronidase at 1 U/ml of resuspended synovial fluid. The digest was loaded on a DEAE column (Whatman International, Maidstone, UK) settled volume of 300 ml, equilibrated with NaAc buffer, 50 mM and washed with 1.5 L of the same buffer. The material with lubricating activity was eluted off of the DEAE matrix with 1 M NaCl. A 1 L wash was collected and concentrated via a 500 ml Amicon flow cell with an XM-100 membrane (mw cutoff 100 kDa). The concentrated sample was dialyzed against 25 mM phosphate buffer, pH 7.4, containing 0.15 M NaCl and 0.5 mM $CaCl_2$.

The DEAE-bound concentrate was loaded onto a peanut agglutinin (PNA)-agarose affinity column with a settled bed volume of 25 ml, equilibrated at room temperature with 25 mM phosphate and 0.15 NaCl buffer, pH 7.4. Unbound protein was eluted with the same buffer until absorbance at 230 and 280 nm decreased to background. Material with lubricating activity was maximally eluted in the presence of a step-wise gradient of α-lactose at a concentration of 0.07 M in 25 mM Tris and 0.15 M NaCl at pH 7.4. This material was loaded onto an Actigel ALD agarose (Sterogene Bioseparations, Arcadia, Calif.) coupled via amine groups to a murine monoclonal antibody against human fibronectin (Zymed Laboratories Inc., San Francisco, Calif.) to remove fibronectin as a contaminant. Eluted material was assayed for purity on SDS-PAGE (5–15% acrylamide) stained with Coomassie blue and by HPLC.

Protein electrophoresis standards were from GibcoBRL (Grand Island, N.Y.), and DNA ladder standard was from FMC Bioproducts (Rockland, Me.).

High Pressure Liquid Chromatography

A Bondpak C18 3.9×150 mm column (Waters, Milford, Mass.) was eluted in reverse phase with 45% (v/v) methanol (Sigma) and 5% (v/v) acetonitrile (Aldrich) HPLC grade at 1 ml/min at 35° C. The eluate was assayed by a photo diode array detector PDA 996 (Waters), and material in peak fractions were analyzed by purity plots calculated using Millenium 32 software (Waters).

Friction Apparatus

A standard friction apparatus (e.g., an apparatus described by Jay et al., 1992, Conn. Tiss. Res. 28:71–88 or Jay et al., 1998, J. Biomed. Mater. Res. 40:414–418) was used to measure lubricating activity. Natural latex was oscillated against a ring of polished glass with a constant contact area of 1.59 cm². The bearing system was axially loaded within a gimbals system free to rotate around two perpendicular horizontal axes. Latex and glass as bearing materials were chosen because they offer a flat surface with small asperity heights on the order of 0.05 mm. Latex, like cartilage, is compliant. Within the gimbals system, these surfaces possess near perfect co-planarity. Accordingly, fluid wedges were not generated and only a thin layer of boundary fluid was present. The entraining velocity (i.e., sliding speed) was 0.37 mm/sec with a constant contact pressure of $0.35 \times 10^6$ N/m².

The friction apparatus recorded displacements of the gimbals system around the vertical loading axis through a linear displacement voltage transducer, the output voltage of which was directly proportional to the magnitude of the frictional torque. The peak to peak amplitude of this signal was related to $\mu$ by a previous calibration with known frictional torque.

Test surfaces were cleaned extensively before use. A 3.8×3.8 cm piece of latex strapped onto the stainless steel stud was washed under running distilled deionized water (DDW) for 2 mm. It was then placed in a shallow bath of 0.9% NaCl physiological saline (PS). The glass slide was scrubbed with a 1% (v/v) 7x detergent (Flow Laboratories, McLean, Va.) solution in DDW for 10 mm and then allowed to soak in the same solution at 100° C. A 5 min. scrubbing was also performed with the hot 7x solution followed by rinsing for 2–4 mm. under running DDW.

The $\mu$ was measured at 35° C. and was preceded by a baseline measurement of the $\mu$ with PS. Lubrication was manifested by a reduction of $\mu$ relative to the $\mu$ of PS. Negative delta $\mu$ values indicate lubrication, whereas positive values indicate friction. Addition of 200 $\mu$l of PS and later 200 $\mu$l of test lubricant was followed by bringing the bearing surfaces close enough so that the solution wet both surfaces. After 5 mm for equilibration, the latex-coated bearing was brought to rest on the glass as it was oscillating. Peak to peak voltages were automatically recorded after 1, 3 and 5 mins. At this point, the surfaces were separated for 2 min. and then brought back together for another 5 mm session. The 3 and 5 min. $\mu$ values of the last two 5 min. sessions typically stabilized and were recorded.

Human serum fibronectin was purchased from Sigma Chemical (F0895, St. Louis, Mo.) and dialyzed against PS before use in the friction apparatus.

Boundary lubricants exert their effect by changing the physico-chemical characteristics of a surface. Bearing surfaces must generate a mutual repulsion in order to be lubricated in the boundary mode. Typical room temperature examples of boundary lubricants are graphite, teflon and molybdenum sulphide. Such compositions reduce friction between bearing surfaces, and therefore, are used as positive controls in assay to measure the lubricating properties of tribonectins. Tribonectins are boundary lubricants that can have an amphipathic character by coating non-biologic hydrophobic surfaces such as latex. The oligosaccharide component of a tribonectin networks with the surrounding aqueous environment. When the ultimate and penultimate sugars are removed from a naturally-occurring tribonectin purified from synovial fluid, the lubricating ability is eliminated.

The latex:glass arthrotripsometer offers an expedient way to test purified biological lubricating factors repetitively with reproducibility. Natural latex and polished glass represent bearing surfaces with little if any variation in physico-chemical characteristic from test to test. By contrast, resected cartilage apposed to either polished glass or cartilage itself will experience deformation that cannot be accurately controlled. The $\mu$ observed in a cartilage-cartilage bearing lubricated by synovial fluid was between 0.005 and 0.024. The values of $\mu$ in the latex:glass system were appreciably higher and typically 0.04 or less. Differences in $\mu$ between the bearing materials are attributed to the 80% (w/w) water content of cartilage.

Protein Sequencing by Liquid Chromatography and Mass Spectrometry (LCMS)

Standard LCMS was carried out on tryptic digests of the purified lubricating material described above. Excised bands from 2 mm thick 5–20% gradient SDS-PAGE gels (Bio-rad Laboratories, Hercules, Calif.) containing the lubricating material was analyzed. The material was deglycosylated by NaNase III and O-glycosidase DS (Glyko, Novato; Calif.). Deglycosylation was carried out with the above enzymes at activities of 0.17 U/ml and 0.10 U/ml, respectively, for 18 hrs in the presence of 0.5 mg/ml of a tribonectin purified from synovial fluid. In all cases, the gel slices were cut through the middle of the band and were 16 mm³ in size. All contact surfaces were carefully cleaned with 50% (v/v) acetonitrile. Sequence data was entered into the BLAST GENBANK® search algorithm and matches identified.

Isolation and Culture of Human Synovial Fibroblasts

Human synovium with a normal appearance was obtained from a 30 year old white male undergoing arthroscopy. Within 1 hr after surgery, the synovial tissue explant was washed three times with Dulbecco's calcium- and magnesium-free phosphate-buffered saline (GIBCO). Pieces 2 mm³ in size were placed in Dulbecco's modification of Eagle's medium (GIBCO), supplemented with 100 U of penicillin and 100 $\mu$g of streptomycin per ml (GIBCO), containing 4 mg/ml of Clostridiopeptidase A (Worthington Biochemical CLS, 125–200 U/mg) sterilized through a 0.22 mm filter (Nalge). The tissue fragments were further divided with scissors in a 100 mm plastic petri dish (Falcon) and incubated for 4 hrs in 20 ml of medium at 37° C. in a moist atmosphere of 5% carbon dioxide and 95% air.

The digest was well mixed many times by aspiration S into and expulsion from a Pasteur pipette. An equal volume of 0.05% trypsin and 0.02% EDTA in modified Puck's Saline A (GIBCO) were added and incubation continued for a further hour under the same conditions. The suspension was centrifuged 10 min at 400×g at 23° C. and washed three times each with 40 ml of calcium- and magnesium-free phosphate-buffered saline. The pellet was suspended in modified Eagle's medium (20 ml) supplemented with 10% fetal bovine serum (Flow Laboratories), 100 U of penicillin, and 100 mg of streptomycin per ml. Two milliliters of this final mixture were plated per 60 mm plastic petri dish (Falcon). Synovial fibroblasts were grown to confluence and cells harvested. Human skin fibroblasts (American Type Culture Collection (ATCC) Designation CCD-10995K; ATCC, Mannassas, Va.) which served as a control were also grown and harvested using the procedure described above.

RNA Extraction and RT-PCR Analyses

RNA from synovial and skin fibroblasts was purified by RNeasy mini-columns and reagents (Qiagen, Crawley, Ltd., UK). Contaminating genomic DNA was removed by DNAshredder and DNase (RNase free) (Qiagen). First strand cDNA was synthesized by reverse transcription and PCR amplification using the following oligonucleotide primers. MSF-exon 6 forward primer 5'-CCAAACCACCAGTTGTAGATGAAGC-3' (SEQ ID NO:15) and MSF-exon 6 reverse primer-GCGGAAGTAGTCTTCTCTTTTCCATCAG3' (SEQ ID NO:16). These primers correspond to nucleotide position numbers 674–698 and 953–926, respectively, of the human MSF gene (SEQ ID NO:2; GENBANK™ accession number U70136). Thermal cycling conditions were 42° C. for 12 mins., 95° C. for 10 mins., followed by 43 cycles between 94° C.×20 secs and 55–65° C.×30–90 secs. A final extension for 7 mins was at 72° C. (Perkin Elmer Biosystems).

Alternative Splice Variant of MSF is a Tribonectin

A lubricating polypeptide was purified from human synovial fluid using standard biochemical methods followed by affinity chromatography with peanut agglutinin. The final fraction, which solely possessed lubricating ability, contained a product with an apparent molecular weight of 280 kDa. Components with a molecular weight in excess of 280 kDa were not observed. LCMS performed on tryptic fragments from the 280 kDa excised band indicated the presence of two different proteins that matched in the BLAST search algorithm to fibronectin precursor and MSF (GENBANK™ Accession No. U70136). Sequences of MSF were identified from both native and deglycosylated lubricating polypeptides. Accordingly, the purification scheme was terminated with an anti-fibronectin column resulting in the elimination of fibronectin as an impurity (as assayed by C18 analytical HPLC and purity plot analysis). In addition, lower molecular weight bands at 70 and 160 kDa on SDS-PAGE were absent from the purified tribonectin preparation eluting -from the anti-fibronectin column. The purified tribonectin assayed in the friction apparatus was found to display boundary lubricating activity similar to that of whole synovial fluid (Table 5). By contrast, purified serum fibronectin raised friction indicating that synovial fluid lubricating ability was mediated by the purified tribonectin.

TABLE 5

Friction coefficients for a tribonectin purified from human synovial fluid and fibronectin (Mean + SD; N = 3)

| LUBRICANT* | $\mu$ | $\mu$ (PS**) | $\Delta\mu$ |
|---|---|---|---|
| Tribonectin | 0.047 ± .006 | 0.131 ± .007 | −0.084 ± .004 |
| HSF† | 0.040 ± .005 | 0.135 ± .009 | −0.095 ± .011 |
| Fibronectin | 0.181 | 0.136 | +0.045 ± .005 |

*Tested at a concentration of 250 µg/ml in PS.
**Physiological saline.
†Post-mortem human synovial fluid Furthermore, LCMS of tryptic fragments identified portions of exons 6 through 9 of MSF, inclusively. Purified tribonectin reacted to peanut agglutinin indicating the presence of beta (1–3) Gal-GalNAC oligosaccharides by virtue of its purification. An increase in electrophoretic mobility was observed after digestion with NaNase III and O-glycosidase DS, indicating that the purified tribonectin is highly glycosylated via O-linked oligosaccharides. The apparent molecular weight of deglycosylated tribonectin purified from synovial fluid was 120 kDa.

RT-PCR analysis was completed using primers specific for nucleotide sequences encoding the N-terminal end of exon 6 of MSF. RT-PCR's using human synovial fibroblast RNA generated a 280 bp product, the predicted distance between the designed primers. Similar experiments without reverse transcriptase did not generate this product indicating that the RNA was free of genomic DNA. Purified RNA from skin fibroblasts did not produce any product using the same primers.

MSF was first isolated from human monocytes; a 25 kDa fragment of MSF was found to stimulate the development of megakaryocytes. MSF precursor protein is 1404 residues in size and constructed from 12 exons. Exon 6 appears to encodes a centrally located mucin that is 940 residues in length. Exon 6 has homology to vitronectin, exons 2 and 3 appear homologous to somatomedin B-like regions, and exons 8, 9 are similar to hemopexin-like regions in vitronectin. Hemopexin is a serum heme scavenging protein that interacts with hyaluronate.

A tribonectin purified from synovial fluid and an articular cartilage superficial zone protein (SZP) purified from articular cartilage share sequence identity with MSF but differ in their apparent molecular weights and amino acid sequences.

EXAMPLE 1

MSF Gene Expression by Human Synovial Fibroblasts

A naturally-occurring tribonectin was found to be expressed by human synovial fibroblasts from a gene encoding MSF. Some, but not all, of the exons of the MSF gene are represented in the tribonectin gene product. For example, the tribonectin contains sequences encoded by exons 6–9 of the MSF gene, but lacks sequences encoded by at least one exon of the naturally-occurring MSF gene.

MSF gene expression was evaluated as follows. Gel slices from the 240 kDa apparent molecular weight band of purified tribonectin from pooled human synovial fluids with normal lubricating ability were digested with trypsin. N-terminal sequencing of tryptic fragments was performed by liquid chromatography mass spectrometry and results compared to known sequences in GenBank™. Digestion of purified tribonectin with O-glycosidase DS and NaNaseIII was used to indicate the molecular weight of the core protein. Lubricating ability was assayed using a standard friction apparatus that oscillates natural latex against a ring of polished glass.

Two previously identified protein species were present in the final lubricating fraction of human synovial fluid. Tryptic fragments from fibronectin precursor (FN) and megakaryocyte stimulating factor (MSF) were both identified. A 100% match (E values range 0.31–0.047) was observed with MSF sequences specific for exons 6 though 9. MSF is 1104 amino acids in size with multiple functional domains- similar to vitronectin. This tribonectin reduced the coefficient of friction ($\mu$) from 0.142 to 0.036 whereas purified serum fibronectin raised $\mu$ from 0.136 to 0.181. Forward and reverse RT-PCR primers corresponding to amino acid positions 214–222 and 300–309 of SEQ ID NO:1 were used to probe purified mRNA from human synovial fibroblasts grown in vitro. A 280 bp gene product was observed consistent with the predicted amino acid sequence. The data described herein indicate that a naturally-occurring tribonectin is secreted by synovial fibroblasts via expression of the MSF gene.

The methods described below were used to characterized a lubricating component in synovial fluid.

Human Synovial Fluid Collection

Aliquots of synovial fluid from patients undergoing diagnostic arthroscopy and total knee replacement were collected and assayed in the friction apparatus. In both cases, the synovial fluid was aspirated prior to initiation of any surgical procedure and immediately centrifuged at 10,000×g at 4° C. for 2 hrs to remove cellular debris. Samples that were grossly contaminated with blood were discarded. Aliquots with normal lubricating ability were pooled and stored at −20° C.

Purification and Isolation of Human Tribonectins

Human synovial fluid 200 ml was filtered through 0.22 $\mu$m sterile filter units (Nalgene) at 4° C. over two days. Retentate was scraped off filter membranes and resuspended with 50 mM NaAc buffer, pH 5.5, to the original synovial fluid volume. The resuspension buffer contained proteolytic inhibitors: 1 mM PMSF, 1 mM PCMB and 10 mM EDTA. Digestion of hyaluronic acid was carried out at 37° C. by streptomyces hyaluronidase at 1 U/ml of resuspended synovial fluid. The digest was loaded on a DEAE column (Whatman International, Maidstone, UK) settled volume of 300 ml, equilibrated with NaAc buffer, 50 mM and washed with 1.5 L of the same buffer. The desired material was eluted from the DEAE matrix with 1 M NaCl. A 1 L wash was collected and concentrated via a 500 ml Amicon flow cell with an XM-100 membrane (mw cutof=100 kDa). The concentrated sample was dialyzed against 25 mM phosphate buffer, pH 7.4, containing 0.15 M NaCl and 0.5 mM $CaCl_2$.

The DEAE-bound concentrate was loaded onto a peanut agglutinin (PNA)-agarose affinity column with a settled bed volume of 25 ml, equilibrated at room temperature with 25 mM phosphate and 0.15 NaCl buffer, pH 7.4. Unbound protein was eluted with the same buffer until absorbance at 230 and 280 nm decreased to background. Desired material was maximally eluted in the presence of a step-wise gradient of $\alpha$-lactose at a concentration of 0.07 M in 25 mM Tris and 0.15 M NaCl at pH 7.4. Pre-purified tribonectin was loaded onto an Actigel ALD agarose (Sterogene Bioseparations, Arcadia, Calif.) coupled via amine groups to a murine monoclonal antibody against human fibronectin (Zymed Laboratories Inc., San Francisco, Calif.). Eluted material was assayed on SDS-PAGE 5–15% stained with Coomassie blue and by HPLC.

High Pressure Liquid Chromatography

A $\mu$Bondapak C18 3.9×150 mm column (Waters, Milford, Mass.) was eluted in reverse phase with 45% (v/v) methanol (Sigma) and 5% (v/v) acetonitrile (Aldrich) HPLC grade at 1 ml/min at 35° C. Eluate was assayed by a photo diode array detector PDA 996 (Waters) and peaks analyzed by purity plots calculated using Millenium 32 software (Waters).

Friction Apparatus

A standard friction apparatus was used to measure lubricating activity as described above The $\mu$ was measured at 35° C. and was preceded by a baseline measurement of the $\mu$ with PS. Lubrication was manifested by a reduction of $\mu$ relative to the $\mu$ of PS. Negative $\Delta\mu$ values indicate lubrication whereas positive values indicate friction. Addition of 200 $\mu$l of PS and later 200 $\mu$l of test lubricant was followed by bringing the bearing surfaces close enough so that the solution wet both surfaces. After 5 min for equilibration, the latex-coated bearing was brought to rest on the glass as it was oscillating. Peak to peak voltages were automatically recorded after 1, 3 and 5 mins. At this point the surfaces were separated for 2 min and then brought back together for another 5 min session. The 3 and 5 min $\mu$ values of the last two 5 min sessions typically stabilized and were recorded.

LCMS

LCMS of tryptic digests was carried out as described above. Bands were excised from 2 mm thick 5–20% gradient SDS-PAGE gels (Bio-rad Laboratories, Hercules, Calif.) for further analysis. Deglycosylation was carried out using NaNase III and O-glycosidase DS (Glyko, Novato, Calif.) (at concentrations of 0.17 U/ml and 0.10 U/ml, respectively, for 6 hrs in the presence of 0.5 mg/ml of protein. In all cases, the gel slices were cut through the heart of the band and were 16 $mm^3$ in size. All contact surfaces were carefully cleaned with 50% (v/v) acetonitrile. Sequence data was entered into the BLAST GenBank™ search algorithm and matches identified.

RNA Extraction and RT-PCR Analyses

RNA from synovial and skin fibroblasts was purified by RNeasy mini-columns and reagents (Qiagen, Crawley, Ltd., UK). Contaminating genomic DNA was removed by DNAshredder and DNase (RNase free) (Qiagen). First strand cDNA was synthesized by reverse transcription and PCR amplification using the following oligonucleotide primers: MSF-exon 6 forward primer 5'-CCAAACCACCAGTTGTAGATGAAGC-3' (SEQ ID NO:15) and MSF-exon 6 reverse primer 5'-GCGGAAGTAGTCTTCTCTTTTCCATCAG-3' (SEQ ID NO:16). These primers correspond to base pair position numbers 674–698 and 953–926 respectively in GENBANK™ Acession number U70136 (human MSF). Thermal cycling conditions were 42° C. for 12 mins, 95° C. for 10 mins followed by 43 cycles between 94° C.×20 secs and 55–65° C.×30–90 secs. A final extension for 7 mins was at 72° C. (Perkin Elmer Biosystems).

Miscellaneous Reagents

Human serum fibronectin was purchased from Sigma Chemical (F0895, St. Louis, Mo.) and dialyzed against PS before use in the friction apparatus. Protein electrophoresis standards were from GibcoBRL (Grand Island, N.Y.) and DNA ladder standard was from FMC Bioproducts (Rockland, Me.).

A tribonectin from from human synovial fluid was purified. The final fraction which solely possessed lubricating ability primarily contained a product with an apparent molecular weight of 280 kDa. The fraction also contained minor low molecular weight components, which were removed with the final antibody-based purification step. Components with a molecular weight in excess of 280 kDa were not observed. LCMS performed on tryptic fragments from the 280 kDa excised band indicated the presence of two different proteins that matched in the BLAST search algorithm to fibronectin precursor and MSF (GENBANK™ Accession No. U70136). Sequences of MSF were identified from both native and deglycosylated tribonectin. Accordingly, the purification scheme was terminated with an anti-fibronectin column resulting in the near elimination of fibronectin as an impurity on the basis of C18 analytical HPLC and purity plot analysis. In addition, the minor low molecular weight bands at 70 and 160 kDa on SDS-PAGE were absent from the purified preparation eluting from the anti-fibronectin column. Purified tribonectin assayed in the friction apparatus was found to display boundary lubricating activity similar to that of whole synovial fluid (Table 6).

TABLE 6

Friction coefficient for a human tribonectin and fibronectin

| LUBRICANT† | $\mu$ | $\mu$ (PS*) | $\Delta\mu$ |
| --- | --- | --- | --- |
| Tribonectin | 0.035 | 0.142 | −0.106 |
| Fibronectin | 0.181 | 0.136 | +0.045 |

*Physiological saline.
†Tested at a concentration of 250 $\mu$g/ml in PS.

In contrast, purified serum fibronectin raised friction indicating that synovial fluid lubricating ability was mediated by tribonectin.

LCMS of tryptic fragments correctly identified portions of exons 6 through 9 of MSF inclusively. Fragments encoded by nucleic acid sequences at the beginning and end of exon 6 were found. The tribonectin reacted to PNA indicating the presence of β(1–3)Gal-GalNAC oligosaccharides by virtue of its purification. In addition there was a very significant increase in electrophoretic mobility after digestion with NaNase III and O-glycosidase DS indicating that the tribonectin is highly glycosylated via O-linked oligosaccharides. The apparent molecular weight of deglycosylated tribonectin was 120 kDa.

RT-PCR analysis was completed using primers specific for nucleotide sequences encoding the N-terminal end of exon 6 of MSF. RT-PCR's using human synovial fibroblast RNA generated a 280 bp product, the predicted distance between the designed primers. Similar experiments without reverse transcriptase did not generate this product indicating that the RNA was free of genomic DNA. Purified RNA from skin fibroblasts did not produce any product using the same primers.

The data described herein indicate that the exons of the MSF gene are alternatively spliced to express lubricating polypeptides in synovial joints. Synovial fibroblasts are one of the the sources of such tribonectins in joints. An isolated naturally-occurring tribonectin described herein (Mr~280 kDa) and SZP (Mr~345 kDa) are different molecules as they differ in apparent molecular weight by 65 kDa. It is possible that MSF is a precursor for both molecules by virtue of differing expression of MSF exons by two independent cell lines that populate the synovial cavity. Repetitive LCMS sequencing of tryptic digests did not identify any of the exons which bracket exons 6 through 9 in MSF. A naturally-occurring tribonectin purified from bovine calf was found to have the same molecular weight as a tribonectin purified from the human sources.

Boundary lubricants exert their effect by changing the physico-chemical characteristics of a surface. Bearing surfaces must generate a mutual repulsion in order to be lubricated in the boundary mode. Commonplace room temperature examples are graphite, teflon and molybdenum sulphide. Tribonectins appear to have an amphipathic character by coating non-biologic hydrophobic surfaces such as latex. The extensive glycosylations are important to network with the surrounding aqueous environment. When the ultimate and penultimate sugars are removed the lubricating ability is eliminated. The possibility of hyaluronate binding to SZP or a tribonectin via protein expressed by exon 9 supports a mechanism by which hyaluronate plays a role in synovial fluid. A hyaluronate polymer may serve to bind many SZP or tribonectin molecules in tandem side-by-side, thus distributing shear stress and stabilizing lubricant molecules.

The primary structure of MSF precursor (alternatively spliced gene products such as tribonectins) is different from that of MG2, statherine, and proline rich glycoprotein which are found in saliva and lubricate dental bearings. Only MG2 has been tested in the present latex:glass bearing and found to lubricate as effectively as a tribonectin. Both glycoproteins share the same O-linked β(1–3)Gal-GalNAc moiety. These data indicate that the O-linked β(1–3)Gal-GalNAc moiety is important for boundary lubrication activity.

Enzymatic digestion experiments indicate that boundary lubrication provided by synovial fluid is highly sensitive to trypsin. These experiments demonstrated that the removal of lubricating ability by phospholipases (contaminated with very small amounts of trypsin-like proteases) could be eliminated by co-incubation with protease inhibitors, leupeptin and aprotinin. Lysine and arginine comprises 13.5% and 1.3% respectively of the exon 6 product which supports the observation of trypsin sensitivity, even though this is the same region of tribonectin that is extensively glycosylated and could therefore prevent proteolysis. It is likely that even minor inflammatory states that elaborate trypsin or elastase have deleterious effects upon the lubricating ability of naturally-occurring tribonectins. Non-lubricated cartilaginous bearings may experience premature wear which can initiate osteoarthritis. Such conditions are treated using the lubricating polypeptides, i.e., tribonectins, described herein.

EXAMPLE 2

Homology of a Tribonectin and SZP: Products of MSF Gene Expression by Human Synovial Fibroblasts and Articular Chondrocytes Localized to Chromosome 1q25

Expression of tribonectins was evaluated in primary human synovial fibroblasts and primary articular cartilage. RNA was purified from human synovial fibroblasts and articular chondrocytes grown in vitro from tissue explants obtained from subjects without degenerative joint disease. RT-PCR was used with multiple complimentary primer pairs spanning the central mucin expressing exon 6 of the MSF gene and individual exons on both the N- and C-terminal sides of exon 6. Exons 2, 4 and 5 appear to be variably expressed by synovial fibroblasts and articular chondrocytes. A lubricating polypeptide, a tribonectin, expressed from various exons of the MSF gene is expressed by both chondrocytes and synovial fibroblasts in vitro. Both a tribonectin and superficial zone protein (SZP), a related proteoglycan, share a similar (but not identical) primary structure. Tribonectins and SZP also differ in post-translational modifications with O-linked oligosaccharides; tribonectins contain O-linked oligosaccharides, whereas such post-translational modifications have not been detected in SZP. The oligosaccharides are predominant in tribonectins; limited amounts of chondroitin and keratan sulfate are found in SZP. Since most of the MSF exons are involved in the expression of a tribonectin, a strong homology to vitronectin persists. Screening of a human genome BAC library with a cDNA primer pair complimentary for exon 6 identified two clones. Both clones were complimentary for chromosome 1q25 by in situ hybridization. This locus was implicated in camptodactyl-arthropathy-pericarditis syndrome (CAP) by genetic mapping. CAP, a large joint arthropathy, is associated with ineffective boundary lubrication provided by synovial fluid. Accordingly, the tribonectins described herein are useful to prevent and/or treat CAP.

The data described below addresses the following questions: 1) Which of the 12 MSF exons are expressed by synovial fibroblasts and presumably result in tribonectin secretion into the synovial cavity, 2) how does this differ from the expression of MSF by articular chondrocytes which results in SZP secretion onto the surface of cartilage, 3) do tribonectins and SZP share the same primary structure, 4) are tribonectins post-translationally modified with chondroitin sulfate- a feature of SZP, and 5) does an isolated exon 6 product possess boundary lubricating ability.

Human synovial fluid was collected and processed as described above, and tribonectins were purified and isolated from human tissue using methods described above. Lubricating activity was measured using a standard friction apparatus.

Immunodetection of Chondroitin-6-Sulfate

Monoclonal antibody M621 C. (ICN, Aurora, Ohio) was use to detect the presence of chondroitin-6-sulfate in purified tribonectin. Standard dot and Western blotting techniques were used.

Digestion of a Tribonectin with Chymotrypsin

TLCK-treated chymotrypsin 0.1BTEE U/ml of human synovial fluid was incubated for 1 hr at 37° C. Immediately following digestion lubricating activity was assayed in the friction apparatus. Additional digestions were carried out in the same way but also in the presence of 10 μg/ml leupeptin and 5 μg/ml aprotinin in the event that commercial TLCK treatment incompletely inactivated contaminating trypsin.

Isolation and Culture of Human Articular Chondrocytes

In addition to isolating human synovial fibroblasts as described above, human chondrocytes were isolated. Cartilage from the femoral condyles and tibial plateaus of human knee joints was obtained at autopsy from donors without known history of joint disease or from healthy organ donors from tissue banks. Cartilage slices were cut into 2–3mm³ pieces, washed with DMEM (Whittaker MAB Bioproducts, Walkerville, Md.) and treated for 15 min with trypsin 10% (v/v) in a 37° C. waterbath. The tissues were transferred to DMEM, 5% FBS, penicillin-streptomycin-fungizone, and 2 mg/ml *C. perfringens* collagenase type IV (Sigma) and digested overnight on a gyratory shaker. The cells were washed 3 times with DMEM and cultured in DMEM containing 5% FBS.

Culture of Human Monocytes

Human monocytes CRL-9855 in suspenson were purchased from American Type Culture Collection (Mannassas, Va.). Cells were concentrated by centrifugation and then resuspended in a T75 flask to concentration between 0.2 and $1.0 \times 10^6$/ml with Iscove's modified Dulbecco's medium supplemented with 10% fetal bovine serum that was not heat inactivated (Flow Laboratories), 0.03 mM thymidine, 0.1 mM hypoxanthine and 0.05 mM 2-mercaptoethanol. As the monocytes multiplied, the culture was expanded to maintain the above concentration range.

RNA Extraction and RT-PCR Analyses

RNA from human synovial and articular chondrocytes and monocytes were purified by RNeasy mini-columns and reagents (Qiagen, Valencia, Calif.). Contaminating genomic DNA was removed by DNAshredder and DNase (RNase free) (Qiagen). Complimentry DNA synthesis was done by incubating at 25° C. for 10 min for extension of hexameric primers by reverse transcriptase, and synthesis of cDNA at 42° C. for 12 min, and activation of Ampli Taq/denaturation of RNA-cDNA complex at 95 C for 10 min. Thermal cycling condition was 43 cycles of 94° C., 20 secs for denaturation and 62° C., 60 secs, and a final extension at 72° C. for 7 mins (Perkin Elmer Biosystems, Foster City, Calif.). RT-PCR products were analyzed by 3% NuSieve GTG agarose (FMC, Rockland, Me.) gel electrophoresis stained with ethidium bromide. Bands not corresponding to expected RT-PCR product sizes were excised and extracted from agarose (Qiagen).

BAC Clone Library Screening

An *E. coli* BAC library containing the human genome was screened (Research Genetics Inc., Huntsville, Ala.) with a cDNA primer pair complimentary to MSF exon 6 by PCR. Forward primer 5'-CCAAACCACCAGTTGTAGATGAAGC-3' (SEQ ID NO:15) and reverse primer 5'-GCGGAAGTAGTCTTCTCTTTTCCATCAG-3' (SEQ ID NO:16) complimentary to base pair position numbers 674–698 and 953–926 of SEQ ID NO:2. Candidate *E. coli* clones were grown in LB agar containing 12.5 mg/ml chloramphenicol at 37° C. for 16 hrs. Large construct DNA free of genomic DNA was purified by anion exchange and exonuclease digestion (Qiagen Large-construct kit, Valencia, Calif.).

In situ Hybridization of BAC Clone DNA and Chomosomes

Metaphase chromosomes were prepared from short term lymphocyte cultures from a normal individual according to established protocols. Two micrograms of BAC DNA from positive clones were labeled using BioNick labeling kit (Life Technologies, Md.) using biotin 14-dATP in a nick translation reaction according to a protocol supplied by the manufacturer. After nick translation, the reaction products were purified on a G-50 column. 100 ng of labeled DNA and 20 μg of cot1 DNA were co-precipitated with ethanol. The DNA was recovered by centrifugation and dissolved in 20 μl of hybridization solution (Hybrisol vii, Oncor). Probe hybridization, washing, microscopy and mapping of the probes were performed according to standard procedures.

Digestion of Tribonectins with Chymotrypsin and Assay for Lubricating Ability

A tribonectin was purified from pooled human synovial fluid with normal lubricating ability defined as $\Delta\mu$<–0.06 and possessed an apparent molecular weight of 280 kDa. Terminating the purification with an anti-fibronectin step was carried out to remove contaminating bands. This step also reduced the purity angle to <6°. A tribonectin at a concentration of 250 μg/ml lubricated the latex:glass bearing as effectively as post-mortem synovial fluid from a subject without degenerative joint disease (Table 7).

TABLE 7

Friction coefficients for human a human tribonectin and fibronectin

| Lubricant | $\mu$ | $\mu$ (PS‡) | $\Delta\mu$ | N |
|---|---|---|---|---|
| Tribonectin† | 0.047 ± .006 | 0.131 ± .007 | –0.084 ± .004 | 3 |
| HSF* | 0.040 ± .005 | 0.135 ± .009 | –0.095 ± .011 | 3 |
| Chmyotrypsin§ | 0.130 ± .041 | 0.107 ± .024 | +0.02 ± .035 | 3 |

Mean ± SD
†Tested at a concentration of 250 μg/ml in PS.
‡Physiological saline
*Post-mortem human synovial fluid
§HSF digested with TLCK-treated chymotrypsin in the presence of leupeptin and aprotinin.

Enzymatic digestions with TLCK-treated chymotrypsin were performed to determine if the isolated exon 6 protein product possesses lubricating ability as this domain does not contain aromatic amino acids. The resulting digestate raised μ to 0.130 from the saline control value μ□=0.107. Similar digestions in the presence of leupeptin/aprotinin continued to demonstrate no lubricating ability ($\Delta\mu$=+0.02).

Immunodetection of Chondrotin-6-Sulfate

Monoclonal antibody M621C was used to probe tribonectins transferred to nitrocellulose.

No reaction was observed corresponding to the 280 kDa band on the original SDS-PAGE. This indicates that tribonectins do not contain chondroitin-6-sulfate.

RT-PCR Analysis of Synovial Fibroblast and Articular Chondrocyte RNA

RT-PCR of chondrocyte and synovial fibroblast mRNA was carried out using the primers illustrated in Table 8. RT-PCR products of the predicted size in addition to others that were smaller than predicted were observed for both cell lines. The primer pair spanning the C-terminal end of exon 6 to the N-terminal end of exon 12 was observed to be 769 bp, its predicted length, for both cell lines. Similarly, the primer pair spanning the same position in exon 6 to exon 11 produced an expected RT-PCR product of 654 bp. The primer pair of exon 5 and 6 produced the expected RT-PCR product of 278 bp for both cell lines.

TABLE 8

Primer pairs used in RT-PCR's with RNA from human synovial fibroblasts and articular chondrocytes.

| Inter-exon Primers | Base Pairs | (5'–3') Forward Primer | Base Pairs | (5'–3') Backward Primer |
|---|---|---|---|---|
| 1–6 | 64–85 | TTGTTGCTGCTGTCTGTTTTCG (SEQ ID NO:17) | 819–796 | GGGTCTGGGATTTATTGGTTTTGC (SEQ ID NO:23) |
| 2–6 | 128–149 | GGAGATGTGGGGAAGGGTATTC (SEQ ID NO:18) | 819–796 | GGGTCTGGGATTTATTGGTTTTGC (SEQ ID NO:24) |
| 4–6 | 371–394 | CACCATCTTCAAAGAAAGCACCTC (SEQ ID NO:19) | 819–796 | GGGTCTGGGATTTATTTGGTTTTGC (SEQ ID NO:25) |
| 5–6 | 542–566 | CCTCCTCTTCCTCTTCTTCTTCAAC (SEQ ID NO:20) | 819–796 | GGGTCTGGGATTTATTGGTTTTGC (SEQ ID NO:26) |
| 6–11 | 3427–3448 | GGCATTATCATCAATCCCATGC (SEQ ID NO:21) | 4080–4057 | CACATTTGGAAGTCCTCTCCACAG (SEQ ID NO:27) |
| 6–12 | 3427–3448 | GGCATTATCATCAATCCCATGC (SEQ ID NO:22) | 4195–4171 | TTGCTCTTGCTGTTCTACTAGGCAC (SEQ ID NO:28) |

Base pair position numbers correspond to accession number U 70136 in GENEBANK™.

TABLE 9

Primer pairs used in RT-PCR's with RNA from human monocytes.

| Inter-exon Primers | Base Pairs | (5'–3') Forward Primer | Base Pairs | (5'–3') Backward Primer |
|---|---|---|---|---|
| 1–3 | 64–85 | TTGTTGCTGCTGTCTGTTTTCG (SEQ ID NO:29) | 313–291 | CATACTTCTTACATTGGGTCG (SEQ ID NO:32) |
| 1–4 | 64–85 | TTGTTGCTGCTGTCTGTTTTCG (SEQ ID NO:30) | 375–354 | TGGTGGTGATGTGGGATTGC (SEQ ID NO:33) |
| 2–5 | 128–149 | GGAGATGTGGGGAAGGGTATTC (SEQ ID NO:31) | 540–517 | GGAGGAGGAGGACTCTTGTTTTC (SEQ ID NO:34) |

Base pair position numbers correspond to accession number U 70136 in GENBANK™.

The primer pair spanning from exon 1 to exon 6 failed to singularly generate the predicted product size of 756 bp. Instead three smaller sized (350, 450 and 490 bp) bands were observed for both cell lines. The primer pair spanning from exon 2 to the exon 6 N-terminus produced a product roughly 420 bp in size for both cell lines and was 272 bp (692 bp–420 bp) shorter than its predicted size. The predicted RT-PCR 692 bp product was faintly observed for chondrocytes and less so for synovial fibroblasts. The exon 2 to 6 primer pair 420 bp product was excised and sequenced which revealed the absence of exon 5 and most of exon 4 except for the first two N-terminal amino acids Ala$^{105}$ and Leu$^{106}$ of SEQ ID NO:1) Sequencing of the 490 and 450 bp RT-PCR products from the exon 1 to 6 primer pair identified the same deletions. Sequencing of the smaller 350 bp product from the exon 1 to 6 primer pair revealed these same deletions in addition to exon 2 except for the N-terminal Q$^{25}$. The primer pair of exon 4 and 6 produced the expected RT-PCR product of 449 bp for both cell lines and a smaller 340 bp product. Sequencing of this 340 bp product revealed deletion of exon 5 except for the N-terminal E$^{156}$.

Alternative splicing was found to be responsible for generating 4 different phenotypical isoforms of MSF from both synovial fibroblasts and chondrocytes (FIG. 2).

Phenotype V0 consists of all 12 exons, V1 missing exon 5, V2 missing exon 5 and most of 4, and V3 missing exon 5 and most of 4 and 2. Yet another isoform is a polypeptide which contains amino acids encoded by MSF exons 1 and 6–12 (missing exon 5); this is likely the smallest naturally-occurring tribonectin. Each isoform contains the lubricating domain exon 6. The domain encoded by exon 1 plays a role in mediating binding of the tribonectin to hydrophobic surfaces like cartilage.

RT-PCR Analysis of Monocyte RNA

RT-PCRs with purified monocyte RNA using primer pairs (Table 9) complimentary to MSF exon 6 did not produce any products. A primer pair spanning exons 1 to 3, produced a PCR product of 250 bp, its predicted size. Another primer pair spanning exons 1 to 4 produced a PCR product that was approximately 130 bp smaller than the 312 bp predicted size. Yet another primer pair spanning exons 2 to 5 did not generate any PCR product, indicating that exon 5 is not expressed. These data would appear to demonstrate that monocytes express exons 1–3 and do not express exon 6. The forward primer sequence in exon 1 was common to all of the above RT-PCR work involving monocytes, synovial fibroblasts and chondrocytes.

In situ Hybridization of BAC Clone DNA and Chromosomes

Screening of a human genome BAC clone library with the above MSF exon 6 cDNA primer pair resulted in 2 candidate clones. BAC clones 330 and 285 hybridized to chromosome 1 at q25 region (DAPI banding). To confirm the localization to chromosome 1, metaphase chromosomes were hybridized to BAC probes along with chromosome 1 specific centromere probe (VYSIS). Both centromeric as well as the BAC probes hybridized to chromosome 1. Subsequent G-banding of the same slides confirmed the q25 localization.

Synovial fibroblasts grown in vitro alternatively spliced out either MSF exons 2,4 or 5, or a combination thereof. In the case of exon 4, expression stopped after the first two codons of the exon (Ala$^{105}$ and Leu$^{106}$). Isoforms without exon 5 except for residue E$^{156}$ and one without exon 2 except for Q$^{25}$ also exist. Three RT-PCR products occurred with the exon 1 to 6 primer pair which appear to correspond to phenotypes V1–3. However, the expected RT-PCR 692 bp product for the exon 2–6 primer pair was observed, indicating that an isoform V0, which contains each of these exons also exists. It would appear that 4 or 5 different phenotypical isoforms of tribonectins are expressed by synovial fibroblasts. Chondrocytes share this phenotypic expression. A summary of the alternative splice sites for both cell lines is illustrated in FIG. 2. The relatively greater intensity of the 692 bp exon 2–6 and 449 bp exon 4–6 primer products for chondrocytes suggests that these cells could potentially select for a higher molecular weight isotype.

Exon 6 in MSF is positioned between an analogous heparin sulfate binding region (MSF exon 4) and the hemopexin-like repeats (MSF exons 8,9). Separation of these domains encourages greater interaction with glycosaminoglycan which would differ from vitronectin in which these domains are thought to compete for glycosaminoglycan binding due to their proximity. Perhaps the ability to bind to glycosaminoglycan on either or both ends of the lubicating domain serves to stabilize lubricating activity on cartilage covered with the lamina splendins. Alternatively, an interaction exists between a tribonectin and collagen type II, which interaction serves to bind the tribonectin directly to cartilage.

Boundary lubricants such as tribonectins bind to bearing surfaces and generate a mutual repulsion in order to lubricate in the boundary mode. This bifunctional attribute appears as amphipathic behavior by coating non-biologic hydrophobic surfaces such as latex. Extensive glycosylations network with the surrounding aqueous environment. When ultimate and penultimate sugars are removed the lubricating ability is eliminated. Expression of MSF exon 6 is required for lubricting activity; optimal lubricting activity likely requires the expression of a domain expressed by at least one additional MSF exon, e.g., exon 1. The chymotrypsin digestion experiment carried out was intended to excise the exon 6 product and test this digestate for lubrication assuming that other released exon products would not interfere with lubricating ability. The digestate did not lubricate we;;, despite replication in the presence of leupeptin and aprotinin, suggesting that other exon products may be needed. For example, exon 3, which has a number of cysteine residues which are important in the aggregation of mucin polymers, may be required. The ability of a tribonectin to coat a surface is likely dependent upon hydrophobicity and the ability of individual tribonectin polymers to aggregate.

Immunohistochemical studies failed to detect chondroitin-6-sulfate indicating that it is not present or it is sterically hindered by O-linked glycosylations adjacent to D$^{220}$EASG$^{224}$ where chondroitin sulfate would be attached. The presence of chondroitin and keratan sulfate in SZP was confirmed by $^{35}$S-labeling and release after digestion with keratanase and chondroitin lyase ABC. However, no significant change in SZP molecular weight was observed after this digestion, indicating that only a small amount of substitution was likely. It is possible that either glycosaminoglycan is conjugated to a tribonectin.

TABLE 10

MSF-derivedTribonectin Sequences

Version 1:

Missing exon 5
AA SEQ 1–156 & 200–1404
Nuc SEQ 34–501 & 631–4245

Version 2:

Missing exons 4 and 5
AA SEQ 1–106 & 200–1404
Nuc SEQ 34–351 & 631–4245

Version 3:

Missing exons 2, 4 and 5
AA SEQ 1–25 & 67–106 & 200–1404
Nuc SEQ 34–108 & 232–351 & 631–4245

Version 0:

has all MSF exons

Different stimuli change the balance of various mRNA transcripts/isoforms differing in the exon 2–5 composition. These stimuli distinguish synovial fibroblasts from chondrocytes in regard to how the MSF gene is regulated. The new class of MSF-derived molecules are termed tribonectins. The new nomenclature appropriately identifies lubrication as the salient activity of MSF/lubricin and MSF/SZP given its important location in synovial fluid and apposing cartilaginous bearing surfaces respectively.

These boundary lubricants exert their effect by changing the physico-chemical characteristics of a surface. Boundary lubricants must be able to bind to bearing surfaces and generate a mutual repulsion in order to lubricate in the boundary mode. This bifunctional attribute appears as amphipathic behavior by coating non-biologic hydrophobic surfaces such as latex. A high concentration of an MSF-derived tribonectin is necessary to form a monolayer on natural latex. Previous experiments with the DuNuoy ring in the cyclohexane:0.9% NaCl interface have revealed that interfacial tension decreases significantly at the initial lubricating concentration of 220 mg/ml. Extensive glycosylations network with the surrounding aqueous environment. When ultimate and penultimate sugars are removed the lubricating ability is eliminated. Residues encoded by exon 6 are necessary for lubrication. A domain encoded by exon 3, which has a number of cysteine residues which are important in the aggregation of mucin polymers, is also important for lubricating activity. The ability of lubricin to coat a surface is is dependent upon hydrophobicity and the ability of individual lubricin polymers to aggregate.

Vitronectin is not alternatively spliced as only one mRNA is produced. Each of the 12 exons in MSF are of identical phase indicating that it is a mosaic protein.

Vitronectin is a member of a group of plasma proteins which includes fibrinogen, fibronectin and von Willebrand factor. Vitronectin is a multifunctional regulator of complement and an activator of plasmin. Binding has been observed to collagen type I, hyaluronate, phosphatidylserine, heparin sulfate and the possibility of binding to other glycosaminoglycans also exists. The interaction with glycosaminoglycans is mediated through a putative cationic binding region (vitronectin exon 7) that is near to two hemopexin-like repeats (vitronectin exons 4,5) which also have the capacity to interact with this class of ligand. By contrast, exon 6 in MSF is positioned between an analogous heparin sulfate binding region (MSF exon 4) and the hemopexin-like repeats (MSF exons 8,9). Perhaps the ability to bind to glycosaminoglycan on both ends of the lubricating domain would serve to stabilize lubricating activity on cartilage covered with the lamina splendins.

Immunologic analysis failed to detect chondroitin-6-sulfate indicating that it is not present or it is sterically hindered by O-linked glycosylations adjacent to D220EASG224 where chondroitin sulfate would be attached. The presence of chondroitin and keratan sulfate in SZP was confirmed by $^{35}$S-labeling and release after digestion with keratanase and chondroitin lyase ABC.

SZP and the V1–3 tribonectins described above differ in primary structure and in in post-translational modifications. The presence of the O-linked lubricating moiety b(1–3)Gal-GalNAc has not been demonstrated for SZP as it has for MSF tribonectins. A difference in molecular weight between lubricin/MSF and SZP/MSF has been supported by Western blotting with antibodies developed against SZP purified from superficial zone chondrocytes. A second lower molecular weight band was also observed which was more pronounced when synovial fluid was assayed in the same manner. Glycosaminoglycan (GAG) may be conjugated to MSF-derived tribonectins. Alternatively, the lubricating polypeptides lack GAG.

Camptodactyl-arthropathy Pericarditis Syndrome (CAP)

In situ hydridization experiments indicated that DNA sequences encoding tribonectins reside on chomosome 1q25, as both BAC clone probes independently localized to the same location. A boolean search of Online Mendelian Inheritance in Man (OMIM) revealed one arthritic disease which has been genetically mapped to the same locus. Camptodactyl-arthropathy-pericarditis syndrome (CAP) is characterized by juvenile onset large joint non-inflammatory arthropathy and congenital non-traumatic flexion contractures of one or more inter-phalangeal joints (camptodactyl). The histopathologic appearance of synovial and tenosynovial tissues from patients with this autosomally inherited disease is that of B-type synoviocyte hyperplasia and end-stage fibrosis. CAP syndrome is a direct result of ineffective lubrication resulting in premature joint wear. Some patients with CAP also develop pericarditis. Isolated naturally-occurring or synthetic tribonectins are useful to treat CAP and for lubricating pericardial tissues. CAP is diagnosed by detecting a mutation in the MSF gene.

Other embodiments are within the following claims.

What is claimed is:

1. A composition comprising an isolated lubricating megakaryocyte stimulating factor (MSF) gene product, said gene product consisting of amino acids 67–106 and 200–1140 of SEQ ID NO:1 and at least one O-linked oligosaccharide, wherein said gene product reduces a coefficient of friction between bearing surfaces.

2. A composition comprising an isolated lubricating MSF gene product, said gene product consisting of amino acids 1–25, 67–106, and 200–1404 of SEQ ID NO:1 and at least one O-linked oligosaccharide, wherein said gene product reduces a coefficient of friction between bearing surfaces.

3. A composition comprising an isolated lubricating MSF gene product, said gene product consisting of amino acids 1–156 and 200–1404 of SEQ ID NO:1 and at least one O-linked oligosaccharide, wherein said gene product reduces a coefficient of friction between bearing surfaces.

4. A composition comprising an isolated lubricating MSF gene product, said gene product consisting of amino acids 1–106 and 200–1404 and at least one O-linked oligosaccharide, wherein said gene product reduces a coefficient of friction between bearing surfaces.

5. The composition of claim 1, 2, 3 or 4, wherein said O-linked oligosaccharide is a β(1–3)Gal-GalNAc.

* * * * *

SEQUENCE LISTING

<160> NUMBER OF SEQ ID NOS: 34

<210> SEQ ID NO 1
<211> LENGTH: 1404
<212> TYPE: PRT
<213> ORGANISM: Homo sapiens

<400> SEQUENCE: 1

```
Met Ala Trp Lys Thr Leu Pro Ile Tyr Leu Leu Leu Leu Ser Val
 1               5                  10                  15

Phe Val Ile Gln Gln Val Ser Ser Gln Asp Leu Ser Ser Cys Ala Gly
                20                  25                  30

Arg Cys Gly Glu Gly Tyr Ser Arg Asp Ala Thr Cys Asn Cys Asp Tyr
            35                  40                  45

Asn Cys Gln His Tyr Met Glu Cys Cys Pro Asp Phe Lys Arg Val Cys
        50                  55                  60

Thr Ala Glu Leu Ser Cys Lys Gly Arg Cys Phe Glu Ser Phe Glu Arg
    65                  70                  75                  80

Gly Arg Glu Cys Asp Cys Asp Ala Gln Cys Lys Lys Tyr Asp Lys Cys
                85                  90                  95

Cys Pro Asp Tyr Glu Ser Phe Cys Ala Glu Val His Asn Pro Thr Ser
                100                 105                 110

Pro Pro Ser Ser Lys Lys Ala Pro Pro Ser Gly Ala Ser Gln Thr
            115                 120                 125

Ile Lys Ser Thr Thr Lys Arg Ser Pro Lys Pro Pro Asn Lys Lys Lys
        130                 135                 140

Thr Lys Lys Val Ile Glu Ser Glu Glu Ile Thr Glu Glu His Ser Val
    145                 150                 155                 160

Ser Glu Asn Gln Glu Ser Ser Ser Ser Ser Ser Ser Ser Ser Ser
                    165                 170                 175

Ser Thr Ile Trp Lys Ile Lys Ser Ser Lys Asn Ser Ala Ala Asn Arg
            180                 185                 190

Glu Leu Gln Lys Lys Leu Lys Val Lys Asp Asn Lys Lys Asn Arg Thr
```

```
                195                 200                 205
Lys Lys Lys Pro Thr Pro Lys Pro Pro Val Val Asp Glu Ala Gly Ser
        210                 215                 220

Gly Leu Asp Asn Gly Asp Phe Lys Val Thr Thr Pro Asp Thr Ser Thr
225                 230                 235                 240

Thr Gln His Asn Lys Val Ser Thr Ser Pro Lys Ile Thr Thr Ala Lys
                245                 250                 255

Pro Ile Asn Pro Arg Pro Ser Leu Pro Pro Asn Ser Asp Thr Ser Lys
            260                 265                 270

Glu Thr Ser Leu Thr Val Asn Lys Glu Thr Thr Val Glu Thr Lys Glu
        275                 280                 285

Thr Thr Thr Thr Asn Lys Gln Thr Ser Thr Asp Gly Lys Glu Lys Thr
        290                 295                 300

Thr Ser Ala Lys Glu Thr Gln Ser Ile Glu Lys Thr Ser Ala Lys Asp
305                 310                 315                 320

Leu Ala Pro Thr Ser Lys Val Leu Ala Lys Pro Thr Pro Lys Ala Glu
            325                 330                 335

Thr Thr Thr Lys Gly Pro Ala Leu Thr Thr Pro Lys Glu Pro Thr Pro
            340                 345                 350

Thr Thr Pro Lys Glu Pro Ala Ser Thr Thr Pro Lys Glu Pro Thr Pro
            355                 360                 365

Thr Thr Ile Lys Ser Ala Pro Thr Thr Pro Lys Glu Pro Ala Pro Thr
        370                 375                 380

Thr Thr Lys Ser Ala Pro Thr Thr Pro Lys Glu Pro Ala Pro Thr Thr
385                 390                 395                 400

Thr Lys Glu Pro Ala Pro Thr Thr Pro Lys Glu Pro Ala Pro Thr Thr
            405                 410                 415

Thr Lys Glu Pro Ala Pro Thr Thr Lys Ser Ala Pro Thr Thr Pro Thr
            420                 425                 430

Lys Glu Pro Ala Pro Thr Thr Pro Lys Lys Pro Ala Pro Thr Thr Pro
        435                 440                 445

Lys Glu Pro Ala Pro Thr Thr Pro Lys Glu Pro Thr Pro Thr Thr Pro
450                 455                 460

Lys Glu Pro Ala Pro Thr Thr Lys Glu Pro Ala Pro Thr Thr Pro Lys
465                 470                 475                 480

Glu Pro Ala Pro Thr Ala Pro Lys Lys Pro Ala Pro Thr Thr Pro Lys
            485                 490                 495

Glu Pro Ala Pro Thr Thr Pro Lys Glu Pro Ala Pro Thr Thr Thr Lys
            500                 505                 510

Glu Pro Ser Pro Thr Thr Pro Lys Glu Pro Ala Pro Thr Thr Thr Lys
            515                 520                 525

Ser Ala Pro Thr Thr Thr Lys Glu Pro Ala Pro Thr Thr Thr Lys Ser
        530                 535                 540

Ala Pro Thr Thr Pro Lys Glu Pro Ser Pro Thr Thr Lys Glu Pro
545                 550                 555                 560

Ala Pro Thr Thr Pro Lys Glu Pro Ala Pro Thr Thr Pro Lys Lys Pro
            565                 570                 575

Ala Pro Thr Thr Pro Lys Glu Pro Ala Pro Thr Thr Pro Lys Glu Pro
            580                 585                 590

Ala Pro Thr Thr Thr Lys Lys Pro Ala Pro Thr Ala Pro Lys Glu Pro
            595                 600                 605

Ala Pro Thr Thr Pro Lys Glu Thr Ala Pro Thr Thr Pro Lys Lys Leu
        610                 615                 620
```

-continued

```
Thr Pro Thr Thr Pro Glu Lys Leu Ala Pro Thr Thr Pro Glu Lys Pro
625                 630                 635                 640

Ala Pro Thr Thr Pro Glu Glu Leu Ala Pro Thr Thr Pro Glu Glu Pro
                645                 650                 655

Thr Pro Thr Thr Pro Glu Glu Pro Ala Pro Thr Thr Pro Lys Ala Ala
                660                 665                 670

Ala Pro Asn Thr Pro Lys Glu Pro Ala Pro Thr Thr Pro Lys Glu Pro
            675                 680                 685

Ala Pro Thr Thr Pro Lys Glu Pro Ala Pro Thr Thr Pro Lys Glu Thr
        690                 695                 700

Ala Pro Thr Thr Pro Lys Gly Thr Ala Pro Thr Thr Leu Lys Glu Pro
705                 710                 715                 720

Ala Pro Thr Thr Pro Lys Lys Pro Ala Pro Lys Glu Leu Ala Pro Thr
                725                 730                 735

Thr Thr Lys Glu Pro Thr Ser Thr Thr Ser Asp Lys Pro Ala Pro Thr
            740                 745                 750

Thr Pro Lys Gly Thr Ala Pro Thr Thr Pro Lys Glu Pro Ala Pro Thr
        755                 760                 765

Thr Pro Lys Glu Pro Ala Pro Thr Thr Pro Lys Gly Thr Ala Pro Thr
    770                 775                 780

Thr Leu Lys Glu Pro Ala Pro Thr Thr Pro Lys Lys Pro Ala Pro Lys
785                 790                 795                 800

Glu Leu Ala Pro Thr Thr Thr Lys Gly Pro Thr Ser Thr Thr Ser Asp
                805                 810                 815

Lys Pro Ala Pro Thr Thr Pro Lys Glu Thr Ala Pro Thr Thr Pro Lys
            820                 825                 830

Glu Pro Ala Pro Thr Thr Pro Lys Lys Pro Ala Pro Thr Thr Pro Glu
        835                 840                 845

Thr Pro Pro Pro Thr Thr Ser Glu Val Ser Thr Pro Thr Thr Thr Lys
    850                 855                 860

Glu Pro Thr Thr Ile His Lys Ser Pro Asp Glu Ser Thr Pro Glu Leu
865                 870                 875                 880

Ser Ala Glu Pro Thr Pro Lys Ala Leu Glu Asn Ser Pro Lys Glu Pro
                885                 890                 895

Gly Val Pro Thr Thr Lys Thr Pro Ala Ala Thr Lys Pro Glu Met Thr
            900                 905                 910

Thr Thr Ala Lys Asp Lys Thr Thr Glu Arg Asp Leu Arg Thr Thr Pro
        915                 920                 925

Glu Thr Thr Thr Ala Ala Pro Lys Met Thr Lys Glu Thr Ala Thr Thr
    930                 935                 940

Thr Glu Lys Thr Thr Glu Ser Lys Ile Thr Ala Thr Thr Gln Val
945                 950                 955                 960

Thr Ser Thr Thr Thr Gln Asp Thr Thr Pro Phe Lys Ile Thr Thr Leu
                965                 970                 975

Lys Thr Thr Thr Leu Ala Pro Lys Val Thr Thr Lys Lys Thr Ile
            980                 985                 990

Thr Thr Thr Glu Ile Met Asn Lys Pro Glu Glu Thr Ala Lys Pro Lys
        995                 1000                1005

Asp Arg Ala Thr Asn Ser Lys Ala Thr Pro Lys Pro Gln Lys Pro
    1010                1015                1020

Thr Lys Ala Pro Lys Lys Pro Thr Ser Thr Lys Lys Pro Lys Thr Met
1025                1030                1035                1040
```

-continued

```
Pro Arg Val Arg Lys Pro Lys Thr Thr Pro Thr Pro Arg Lys Met Thr
                1045                1050                1055

Ser Thr Met Pro Glu Leu Asn Pro Thr Ser Arg Ile Ala Glu Ala Met
            1060                1065                1070

Leu Gln Thr Thr Thr Arg Pro Asn Gln Thr Pro Asn Ser Lys Leu Val
        1075                1080                1085

Glu Val Asn Pro Lys Ser Glu Asp Ala Gly Ala Glu Gly Glu Thr
    1090                1095                1100

Pro His Met Leu Leu Arg Pro His Val Phe Met Pro Glu Val Thr Pro
1105                1110                1115                1120

Asp Met Asp Tyr Leu Pro Arg Val Pro Asn Gln Gly Ile Ile Ile Asn
                1125                1130                1135

Pro Met Leu Ser Asp Glu Thr Asn Ile Cys Asn Gly Lys Pro Val Asp
            1140                1145                1150

Gly Leu Thr Thr Leu Arg Asn Gly Thr Leu Val Ala Phe Arg Gly His
        1155                1160                1165

Tyr Phe Trp Met Leu Ser Pro Phe Ser Pro Ser Pro Ala Arg Arg
    1170                1175                1180

Ile Thr Glu Val Trp Gly Ile Pro Ser Pro Ile Asp Thr Val Phe Thr
1185                1190                1195                1200

Arg Cys Asn Cys Glu Gly Lys Thr Phe Phe Lys Asp Ser Gln Tyr
                1205                1210                1215

Trp Arg Phe Thr Asn Asp Ile Lys Asp Ala Gly Tyr Pro Lys Pro Ile
            1220                1225                1230

Phe Lys Gly Phe Gly Gly Leu Thr Gly Gln Ile Val Ala Ala Leu Ser
        1235                1240                1245

Thr Ala Lys Tyr Lys Asn Trp Pro Glu Ser Val Tyr Phe Phe Lys Arg
    1250                1255                1260

Gly Gly Ser Ile Gln Gln Tyr Ile Tyr Lys Gln Glu Pro Val Gln Lys
1265                1270                1275                1280

Cys Pro Gly Arg Arg Pro Ala Leu Asn Tyr Pro Val Tyr Gly Glu Met
                1285                1290                1295

Thr Gln Val Arg Arg Arg Phe Glu Arg Ala Ile Gly Pro Ser Gln
            1300                1305                1310

Thr His Thr Ile Arg Ile Gln Tyr Ser Pro Ala Arg Leu Ala Tyr Gln
        1315                1320                1325

Asp Lys Gly Val Leu His Asn Glu Val Lys Val Ser Ile Leu Trp Arg
    1330                1335                1340

Gly Leu Pro Asn Val Val Thr Ser Ala Ile Ser Leu Pro Asn Ile Arg
1345                1350                1355                1360

Lys Pro Asp Gly Tyr Asp Tyr Tyr Ala Phe Ser Lys Asp Gln Tyr Tyr
                1365                1370                1375

Asn Ile Asp Val Pro Ser Arg Thr Ala Arg Ala Ile Thr Thr Arg Ser
            1380                1385                1390

Gly Gln Thr Leu Ser Lys Val Trp Tyr Asn Cys Pro
        1395                1400
```

<210> SEQ ID NO 2
<211> LENGTH: 5041
<212> TYPE: DNA
<213> ORGANISM: Homo sapiens

<400> SEQUENCE: 2
gcggccgcga ctattcggta cctgaaaaca acgatggcat ggaaaacact tcccatttac    60

-continued

| | |
|---|---|
| ctgttgttgc tgctgtctgt tttcgtgatt cagcaagttt catctcaaga tttatcaagc | 120 |
| tgtgcaggga gatgtgggga agggtattct agagatgcca cctgcaactg tgattataac | 180 |
| tgtcaacact acatggagtg ctgccctgat ttcaagagag tctgcactgc ggagctttcc | 240 |
| tgtaaaggcc gctgctttga gtccttcgag agagggaggg agtgtgactg cgacgcccaa | 300 |
| tgtaagaagt atgacaagtg ctgtcccgat tatgagagtt tctgtgcaga agtgcataat | 360 |
| cccacatcac caccatcttc aaagaaagca cctccaccttt caggagcatc tcaaaccatc | 420 |
| aaatcaacaa ccaaacgttc acccaaacca ccaaacaaga agaagactaa gaaagttata | 480 |
| gaatcagagg aaataacaga agaacattct gtttctgaaa atcaagagtc ctcctcctcc | 540 |
| tcctcctctt cctcttcttc ttcaacaatt tggaaaatca agtcttccaa aaattcagct | 600 |
| gctaatagag aattacagaa gaaactcaaa gtaaaagata acaagaagaa cagaactaaa | 660 |
| aagaaaccta cccccaaacc accagttgta gatgaagctg aagtggatt ggacaatggt | 720 |
| gacttcaagg tcacaactcc tgacacgtct accacccaac acaataaagt cagcacatct | 780 |
| cccaagatca aacagcaaa accaataaat cccagaccca gtcttccacc taattctgat | 840 |
| acatctaaag agacgtcttt gacagtgaat aaagagacaa cagttgaaac taaagaaact | 900 |
| actacaacaa ataaacagac ttcaactgat ggaaaagaga agactacttc cgctaaagag | 960 |
| acacaaagta tagagaaaac atctgctaaa gatttagcac ccacatctaa agtgctggct | 1020 |
| aaacctacac ccaaagctga aactacaacc aaaggccctg ctctcaccac tcccaaggag | 1080 |
| cccacgccca ccactcccaa ggagcctgca tctaccacac ccaaagagcc cacacctacc | 1140 |
| accatcaagt ctgcacccac cacccccaag gagcctgcac ccaccaccac caagtctgca | 1200 |
| cccaccactc ccaaggagcc tgcacccacc accaccaagg agcctgcacc caccactccc | 1260 |
| aaggagcctg cacccaccac caccaaggag cctgcaccca ccaccaa gtctgcaccc | 1320 |
| accactccca aggagcctgc acccaccacc cccaagaagc tgccccaac taccccccaag | 1380 |
| gagcctgcac ccaccactcc caaggagcct acacccacca ctcccaagga gcctgcaccc | 1440 |
| accaccaagg agcctgcacc caccactccc aaagagcctg cacccactgc ccccaagaag | 1500 |
| cctgccccaa ctaccccccaa ggagcctgca cccaccactc caaggagcc tgcacccacc | 1560 |
| accaccaagg agccttcacc caccactccc aaggagcctg cacccaccac caccaagtct | 1620 |
| gcacccacca ctaccaagga gcctgcaccc accactacca gtctgcacc caccactccc | 1680 |
| aaggagcctt cacccaccac caccaaggag cctgcaccca ccactcccaa ggagcctgca | 1740 |
| cccaccaccc ccaagaagcc tgccccaact accccccaagg agcctgcacc caccactccc | 1800 |
| aaggaacctg cacccaccac caccaagaag cctgcaccca ccgctcccaa agagcctgcc | 1860 |
| ccaactaccc caaggagac tgcacccacc accccaaga agctcacgcc caccaccccc | 1920 |
| gagaagctcg cacccaccac ccctgagaag cccgcaccca ccaccctga ggagctcgca | 1980 |
| cccaccaccc ctgaggagcc cacacccacc acccctgagg agcctgctcc caccactccc | 2040 |
| aaggcagcgg ctcccaacac ccctaaggag cctgctccaa ctaccccctaa ggagcctgct | 2100 |
| ccaactaccc ctaaggagcc tgctccaact accccctaagg agactgctcc aactacccct | 2160 |
| aaagggactg ctccaactac cctcaaggaa cctgcaccca ctactcccaa gaagcctgcc | 2220 |
| cccaaggagc ttgcacccac caccaccaag gagcccacat ccaccacctc tgacaagccc | 2280 |
| gctccaacta cccctaaggg gactgctcca actacccta aggagcctgc tccaactacc | 2340 |
| cctaaggagc tgctccaac taccccctaag gggactgctc caactacccct caaggaacct | 2400 |
| gcacccacta ctcccaagaa gcctgccccc aaggagcttg cacccaccac caccaagggg | 2460 |

-continued

```
cccacatcca ccacctctga caagcctgct ccaactacac ctaaggagac tgctccaact    2520 accccaagg agcctgcacc cactacccc aagaagcctg ctccaactac tcctgagaca      2580
cctcctccaa ccacttcaga ggtctctact ccaactacca ccaggagcc taccactatc    2640 cacaaaagcc ctgatgaatc aactcctgag ctttctgcag aacccacacc aaaagctctt    2700
gaaaacagtc ccaaggaacc tggtgtacct acaactaaga ctcctgcagc gactaaacct    2760
gaaatgacta caacagctaa agacaagaca acagaaagag acttacgtac tacacctgaa    2820
actacaactg ctgcacctaa gatgacaaaa gagacagcaa ctacaacaga aaaaactacc    2880
gaatccaaaa taacagctac aaccacacaa gtaacatcta ccacaactca agataccaca    2940
ccattcaaaa ttactactct aaaacaact actcttgcac ccaaagtaac tacaacaaaa     3000
aagacaatta ctaccactga gattatgaac aaacctgaag aaacagctaa accaaaagac    3060
agagctacta attctaaagc gacaactcct aaacctcaaa agccaaccaa agcacccaaa    3120
aaacccactt ctaccaaaaa gccaaaaaca atgcctagag tgagaaaacc aaagacgaca    3180
ccaactcccc gcaagatgac atcaacaatg ccagaattga ccctacctc aagaatagca    3240 gaagccatgc tccaaaccac caccagacct aaccaaactc caaactccaa actagttgaa    3300
gtaaatccaa agagtgaaga tgcaggtggt gctgaaggag aaacacctca tatgcttctc    3360
aggccccatg tgttcatgcc tgaagttact cccgacatgg attacttacc gagagtaccc    3420
aatcaaggca ttatcatcaa tcccatgctt tccgatgaga ccaatatatg caatggtaag    3480
ccagtagatg gactgactac tttgcgcaat gggacattag ttgcattccg aggtcattat    3540
ttctggatgc taagtccatt cagtccacca tctccagctc gcagaattac tgaagtttgg    3600
ggtattcctt cccccattga tactgttttt actaggtgca actgtgaagg aaaaactttc    3660
ttctttaagg attctcagta ctggcgtttt accaatgata taaagatgc agggtacccc     3720 aaaccaattt tcaaaggatt tggaggacta actggacaaa tagtggcagc gctttcaaca    3780
gctaaatata agaactggcc tgaatctgtg tattttttca agagaggtgg cagcattcag    3840
cagtatattt ataaacagga acctgtacag aagtgccctg aagaaggcc tgctctaaat    3900 tatccagtgt atggagaaat gacacaggtt aggagacgtc gctttgaacg tgctatagga    3960
ccttctcaaa cacacaccat cagaattcaa tattcacctg ccagactggc ttatcaagac    4020
aaaggtgtcc ttcataatga agttaaagtg agtatactgt ggagaggact tccaaatgtg    4080
gttacctcag ctatatcact gcccaacatc agaaaacctg acggctatga ttactatgcc    4140
ttttctaaag atcaatacta taacattgat gtgcctagta aacagcaag agcaattact     4200 actcgttctg ggcagacctt atccaaagtc tggtacaact gtccttagac tgatgagcaa    4260
aggaggagtc aactaatgaa gaaatgaata ataaattttg acactgaaaa acattttatt    4320
aataaagaat attgacatga gtataccagt ttatatataa aatgttttt aaacttgaca     4380 atcattacac taaaacagat ttgataatct tattcacagt tgttattgtt tacagaccat    4440
ttaattaata tttcctctgt ttattcctcc tctccctccc attgcatggc tcacacctgt    4500
aaaagaaaaa agaatcaaat tgaatatatc ttttaagaat tcaaaactag tgtattcact    4560
taccctagtt cattataaaa aatatctagg cattgtggat ataaaactgt tgggtattct    4620
acaacttcaa tggaaattat tacaagcaga ttaatccctc ttttttgtgac acaagtacaa    4680 tctaaaagtt atattggaaa acatggaaat attaaaattt tacacttta ctagctaaaa     4740 cataatcaca aagctttatc gtgttgtata aaaaaattaa caatataatg gcaataggta    4800
```

```
gagatacaac aaatgaatat aacactataa cacttcatat tttccaaatc ttaatttgga      4860
tttaaggaag aaatcaataa atataaaata taagcacata tttattatat atctaaggta      4920
tacaaatctg tctacatgaa gtttacagat tggtaaatat cacctgctca acatgtaatt      4980
atttaataaa actttggaac attaaaaaaa taaattggag gcttaaaaaa aaaaaaaaa       5040 a                                                                     5041
```

<210> SEQ ID NO 3
<211> LENGTH: 7
<212> TYPE: PRT
<213> ORGANISM: Homo sapiens

<400> SEQUENCE: 3

Lys Glu Pro Ala Pro Thr Thr
 1               5

<210> SEQ ID NO 4
<211> LENGTH: 5
<212> TYPE: PRT
<213> ORGANISM: Homo sapiens
<220> FEATURE:
<221> NAME/KEY: VARIANT
<222> LOCATION: (1)..(2)
<223> OTHER INFORMATION: Xaa may be any amino acid
<221> NAME/KEY: VARIANT
<222> LOCATION: (5)
<223> OTHER INFORMATION: Xaa may be any amino acid.

<400> SEQUENCE: 4

Xaa Xaa Thr Thr Xaa
 1               5

<210> SEQ ID NO 5
<211> LENGTH: 6
<212> TYPE: PRT
<213> ORGANISM: Homo sapiens

<400> SEQUENCE: 5

Glu Pro Ala Pro Thr Thr
 1               5

<210> SEQ ID NO 6
<211> LENGTH: 6
<212> TYPE: PRT
<213> ORGANISM: Homo sapiens

<400> SEQUENCE: 6

Pro Thr Thr Lys Glu Pro
 1               5

<210> SEQ ID NO 7
<211> LENGTH: 24
<212> TYPE: DNA
<213> ORGANISM: Homo sapiens

<400> SEQUENCE: 7
agatttatca agctgtgcag ggag                                            24

<210> SEQ ID NO 8
<211> LENGTH: 22
<212> TYPE: DNA
<213> ORGANISM: Homo sapiens

<400> SEQUENCE: 8
tttacaggaa agctccgcag tg                                              22

<210> SEQ ID NO 9
<211> LENGTH: 23
<212> TYPE: DNA
<213> ORGANISM: Homo sapiens

<400> SEQUENCE: 9
tcaaggtcac aactcctgac acg                                             23

<210> SEQ ID NO 10
<211> LENGTH: 24
<212> TYPE: DNA
<213> ORGANISM: Homo sapiens

<400> SEQUENCE: 10
ctctcggtaa gtaatccatg tcgg                                            24

<210> SEQ ID NO 11
<211> LENGTH: 22
<212> TYPE: DNA
<213> ORGANISM: Homo sapiens

<400> SEQUENCE: 11
ttgttgctgc tgtctgtttt cg                                              22

<210> SEQ ID NO 12
<211> LENGTH: 24
<212> TYPE: DNA
<213> ORGANISM: Homo sapiens

<400> SEQUENCE: 12
tggataaggt ctgcccagaa cgag                                            24

<210> SEQ ID NO 13
<211> LENGTH: 23
<212> TYPE: DNA
<213> ORGANISM: Homo sapiens

<400> SEQUENCE: 13
tcaaggtcac aactcctgac acg                                             23

<210> SEQ ID NO 14
<211> LENGTH: 24
<212> TYPE: DNA
<213> ORGANISM: Homo sapiens

<400> SEQUENCE: 14
gatggtgtgt gtttgagaag gtcc                                            24

<210> SEQ ID NO 15
<211> LENGTH: 25
<212> TYPE: DNA
<213> ORGANISM: Homo sapiens

<400> SEQUENCE: 15
ccaaaccacc agttgtagat gaagc                                           25

<210> SEQ ID NO 16
<211> LENGTH: 28
<212> TYPE: DNA
<213> ORGANISM: Homo sapiens

<400> SEQUENCE: 16
gcggaagtag tcttctcttt tccatcag                                              28

<210> SEQ ID NO 17
<211> LENGTH: 22
<212> TYPE: DNA
<213> ORGANISM: Artificial Sequence
<220> FEATURE:
<223> OTHER INFORMATION: Description of Artificial Sequence:Forward
      Primer Base Pairs 64-85

<400> SEQUENCE: 17
ttgttgctgc tgtctgtttt cg                                                    22

<210> SEQ ID NO 18
<211> LENGTH: 22
<212> TYPE: DNA
<213> ORGANISM: Artificial Sequence
<220> FEATURE:
<223> OTHER INFORMATION: Description of Artificial Sequence:Forward
      Primer Base Pairs 128-149

<400> SEQUENCE: 18
ggagatgtgg ggaagggtat tc                                                    22

<210> SEQ ID NO 19
<211> LENGTH: 24
<212> TYPE: DNA
<213> ORGANISM: Artificial Sequence
<220> FEATURE:
<223> OTHER INFORMATION: Description of Artificial Sequence:Forward
      Primer Base Pairs 371-394

<400> SEQUENCE: 19
caccatcttc aaagaaagca cctc                                                  24

<210> SEQ ID NO 20
<211> LENGTH: 25
<212> TYPE: DNA
<213> ORGANISM: Artificial Sequence
<220> FEATURE:
<223> OTHER INFORMATION: Description of Artificial Sequence:Forward
      Primer Base Pairs 542-566

<400> SEQUENCE: 20
cctcctcttc ctcttcttct tcaac                                                 25

<210> SEQ ID NO 21
<211> LENGTH: 22
<212> TYPE: DNA
<213> ORGANISM: Artificial Sequence
<220> FEATURE:
<223> OTHER INFORMATION: Description of Artificial Sequence:Forward
      Primer Base Pairs 3427-3448

<400> SEQUENCE: 21
ggcattatca tcaatcccat gc                                                    22

<210> SEQ ID NO 22
<211> LENGTH: 22
<212> TYPE: DNA
<213> ORGANISM: Artificial Sequence
<220> FEATURE:
<223> OTHER INFORMATION: Description of Artificial Sequence:Forward
      Primer Base Pairs 3427-3448

<400> SEQUENCE: 22

```
ggcattatca tcaatcccat gc                                                    22
```

<210> SEQ ID NO 23
<211> LENGTH: 24
<212> TYPE: DNA
<213> ORGANISM: Artificial Sequence
<220> FEATURE:
<223> OTHER INFORMATION: Description of Artificial Sequence:Backward
      Primer Base Pairs 819-796

<400> SEQUENCE: 23

```
gggtctggga tttattggtt ttgc                                                  24
```

<210> SEQ ID NO 24
<211> LENGTH: 24
<212> TYPE: DNA
<213> ORGANISM: Artificial Sequence
<220> FEATURE:
<223> OTHER INFORMATION: Description of Artificial Sequence:Backward
      Primer Base Pairs 819-796

<400> SEQUENCE: 24

```
gggtctggga tttattggtt ttgc                                                  24
```

<210> SEQ ID NO 25
<211> LENGTH: 24
<212> TYPE: DNA
<213> ORGANISM: Artificial Sequence
<220> FEATURE:
<223> OTHER INFORMATION: Description of Artificial Sequence:Backward
      Primer Base Pairs 819-796

<400> SEQUENCE: 25

```
gggtctggga tttattggtt ttgc                                                  24
```

<210> SEQ ID NO 26
<211> LENGTH: 24
<212> TYPE: DNA
<213> ORGANISM: Artificial Sequence
<220> FEATURE:
<223> OTHER INFORMATION: Description of Artificial Sequence:Backward
      Primer Base Pairs 819-796

<400> SEQUENCE: 26

```
gggtctggga tttattggtt ttgc                                                  24
```

<210> SEQ ID NO 27
<211> LENGTH: 24
<212> TYPE: DNA
<213> ORGANISM: Artificial Sequence
<220> FEATURE:
<223> OTHER INFORMATION: Description of Artificial Sequence:Backward
      Primer Base Pairs 4080-4057

<400> SEQUENCE: 27

```
cacatttgga agtcctctcc acag                                                  24
```

<210> SEQ ID NO 28
<211> LENGTH: 25
<212> TYPE: DNA
<213> ORGANISM: Artificial Sequence
<220> FEATURE:
<223> OTHER INFORMATION: Description of Artificial Sequence:Backward
      Primer Base Pairs 4195-4171

<400> SEQUENCE: 28

```
ttgctcttgc tgttctacta ggcac                                                 25
```

<210> SEQ ID NO 29
<211> LENGTH: 22
<212> TYPE: DNA
<213> ORGANISM: Artificial Sequence
<220> FEATURE:
<223> OTHER INFORMATION: Description of Artificial Sequence:Forward
      Primer Base Pairs 64-85

<400> SEQUENCE: 29
ttgttgctgc tgtctgtttt cg                                          22

<210> SEQ ID NO 30
<211> LENGTH: 22
<212> TYPE: DNA
<213> ORGANISM: Artificial Sequence
<220> FEATURE:
<223> OTHER INFORMATION: Description of Artificial Sequence:Forward
      Primer Base Pairs 64-85

<400> SEQUENCE: 30
ttgttgctgc tgtctgtttt cg                                          22

<210> SEQ ID NO 31
<211> LENGTH: 22
<212> TYPE: DNA
<213> ORGANISM: Artificial Sequence
<220> FEATURE:
<223> OTHER INFORMATION: Description of Artificial Sequence:Forward
      Primer Base Pairs 128-149

<400> SEQUENCE: 31
ggagatgtgg ggaagggtat tc                                          22

<210> SEQ ID NO 32
<211> LENGTH: 23
<212> TYPE: DNA
<213> ORGANISM: Artificial Sequence
<220> FEATURE:
<223> OTHER INFORMATION: Description of Artificial Sequence:Backward
      Primer Base Pairs 313-291

<400> SEQUENCE: 32
catacttctt acattgggcg tcg                                         23

<210> SEQ ID NO 33
<211> LENGTH: 22
<212> TYPE: DNA
<213> ORGANISM: Artificial Sequence
<220> FEATURE:
<223> OTHER INFORMATION: Description of Artificial Sequence:Backward
      Primer Base Pairs 375-354

<400> SEQUENCE: 33
tggtggtgat gtgggattat gc                                          22

<210> SEQ ID NO 34
<211> LENGTH: 24
<212> TYPE: DNA
<213> ORGANISM: Artificial Sequence
<220> FEATURE:
<223> OTHER INFORMATION: Description of Artificial Sequence:Backward
      Primer Base Pairs 540-517

<400> SEQUENCE: 34
ggaggaggag gactcttgat tttc                                        24